(12) United States Patent
Falck

(10) Patent No.: US 11,938,338 B2
(45) Date of Patent: Mar. 26, 2024

(54) LIGHT THERAPY SYSTEM AND METHOD

(71) Applicant: KONINKLIJKE PHILIPS N.V., Eindhoven (NL)

(72) Inventor: Thomas Maria Falck, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 652 days.

(21) Appl. No.: 17/047,715

(22) PCT Filed: Apr. 23, 2019

(86) PCT No.: PCT/EP2019/060263
§ 371 (c)(1),
(2) Date: Oct. 15, 2020

(87) PCT Pub. No.: WO2019/206848
PCT Pub. Date: Oct. 31, 2019

(65) Prior Publication Data
US 2022/0047890 A1  Feb. 17, 2022

(30) Foreign Application Priority Data

Apr. 24, 2018 (EP) .................................. 18168982

(51) Int. Cl.
*A61N 5/06* (2006.01)
(52) U.S. Cl.
CPC .... *A61N 5/0618* (2013.01); *A61N 2005/0628* (2013.01); *A61N 2005/0652* (2013.01); *A61N 2005/0663* (2013.01)
(58) Field of Classification Search
CPC .......... A61N 5/0618; A61N 2005/0628; A61N 2005/0652; A61N 2005/0663; A61M 2021/0044; A61M 2021/005; A61M 21/00
See application file for complete search history.

(56) References Cited

U.S. PATENT DOCUMENTS 10,257,902 B2   4/2019   Trouwborst
10,434,280 B2  10/2019   Peeters
(Continued)

FOREIGN PATENT DOCUMENTS

EP    2094064 A1     8/2009
WO  2018197243 A1   11/2018

OTHER PUBLICATIONS

International Search Report dated Jun. 21, 2019.

*Primary Examiner* — Brian T Gedeon
*Assistant Examiner* — Joshua Andrew Schum-Houck

(57) ABSTRACT

A light therapy system (12) for administering a controllable melanopic luminous exposure includes a controllable lighting assembly (16) for use in delivering the desired luminous exposure. The system further includes a visual display means (18) for presenting at the same time a visual output such as a video to the patient. A target melanopic luminous exposure for administration to the patient is received by a controller 24. This target is then adjusted to compensate for an additional melanopic luminous exposure which the visual display means generates in displaying the visual output. A control schedule is then generated for controlling an illuminance of the lighting assembly to deliver over a defined treatment period the adjusted target melanopic luminous exposure. The lighting assembly is then controlled according to the control schedule. In this way both the visual output of the visual display means and the light output of the lighting assembly can be administered, while ensuring that the original target melanopic luminous exposure is delivered and not exceeded.

15 Claims, 5 Drawing Sheets

(56) References Cited

U.S. PATENT DOCUMENTS

| | | |
|---|---|---|
| 10,932,345 B2 | 2/2021 | Schlangen |
| 10,946,211 B2 | 3/2021 | Hommes |
| 2013/0039053 A1 | 2/2013 | Takakura |
| 2013/0040276 A1 | 2/2013 | Takakura |
| 2015/0126806 A1 | 5/2015 | Barroso |
| 2017/0208673 A1* | 7/2017 | Schlangen ............. H05B 47/16 |
| 2018/0043130 A1* | 2/2018 | Moore-Ede ............ H05B 47/16 |

* cited by examiner

LIGHT THERAPY SYSTEM AND METHOD

CROSS-REFERENCE TO PRIOR APPLICATIONS

This application is the U.S. National Phase application under 35 U.S.C. 371 of International Application No. PCT/EP2019/060263, filed on Apr. 23, 2019, which claims the benefit of European Application No. 18168982.9 filed on Apr. 24, 2018. These applications are hereby incorporated by reference herein.

FIELD OF THE INVENTION

This invention relates to a light therapy system and method.

BACKGROUND OF THE INVENTION

It is known that many patients treated in a clinical unit, for example a hospital, and in particular an intensive care unit (ICU), can exhibit a disturbance of their sleeping cycle. This can hamper the healing process of the patient and in particular can increase their risk of developing delirium. Up to 80% of critically ill patients suffer from delirium, resulting in an increased length of stay and in some cases even an increased mortality rate. For this reason, recent guidelines published by critical care societies, namely in the USA and Germany, propose means for prevention of delirium in such patients. The means proposed in particular are non-pharmacological, focusing instead upon attempts to naturally restore the circadian rhythms of patients through bright light therapy.

For humans, exposure of the eyes to light is the most significant factor in synchronizing the circadian rhythm to the natural 24-hour day/night cycle. It is known that by exposing a patient to specially tailored cycles of bright light, synchronized with the cycles of the sun, their circadian rhythm can be re-calibrated and sleep disturbance reduced.

How much light is needed in order to trigger and re-program the circadian rhythm varies depending on a patient's condition and characteristics. In particular, it is known that with increasing age of a person, more light is needed for achieving the same biological effect. Therefore, a clinician has to prescribe a personalized light dosage (in "lux hours").

US 2015/0126806 discloses a lighting system for controlling lighting conditions in a room in accordance with a pre-determined schedule, and in particular in accordance with a circadian rhythm schedule, so as to reduce delirium in a patient. The system includes means for controlling internal light sources and also the amount of external light entering a room in order to adjust the light level or light intensity in the room. The system also comprises light sensors to detect the amount of light that a patient is exposed to.

Developments in light therapy systems for improving sleep patterns in patients are generally sought.

SUMMARY OF THE INVENTION

The invention is defined by the claims.

According to an aspect of the invention, there is provided a light therapy system comprising:
- a lighting assembly operable to create a light output having a controllable illuminance;
- a visual display means for presenting a visual output to a user; and
- a controller, operatively coupled to the lighting assembly and visual display means, and adapted to:
  - receive a data input indicating a target melanopic luminous exposure for administration by the lighting assembly;
  - receive a further data input indicative of one or more luminous characteristics of a visual output intended for presentation by the visual display means;
  - determine based on the further data input an estimated additional melanopic luminous exposure associated with the intended visual output;
  - determine an adjusted target melanopic luminous exposure for administration by the lighting assembly, based on reducing the target melanopic luminous exposure so as to compensate for the additional melanopic luminous exposure;
  - create, based on the adjusted target melanopic luminous exposure, a control schedule for controlling at least the illuminance of the lighting assembly over time such as to deliver in total over a defined treatment period the adjusted target melanopic luminous exposure; and
  - control the lighting assembly in accordance with the control schedule.

The invention is based on a development by the inventors wherein a light therapy system is provided comprising both a lighting assembly for generating a light output and, in addition, a visual display means. The two may preferably be integrated in a single unit, e.g. a single panel. The lighting assembly has at least a controllable illuminance, enabling a controllable amount of light to be administered to a patient. In particular, a dedicated light therapy program can be created for a given patient, configured to deliver a specified target melanopic luminous exposure.

A controller of the light therapy system creates a control schedule for controlling illuminance of the lighting assembly over time such that over the course of a particular time window (the treatment period) the target luminous exposure is delivered.

The target melanopic luminous exposure may for instance be specified by a clinician. The system can hence enable highly efficient technical implementation of a light therapy treatment, based on only minimal input from a clinician.

The further inclusion of a visual display means permits in addition a visual output to be presented to the user. This may for instance be a graphical output by which is meant an output formed for instance of one or more images or moving images. This can be used for example to relax a patient by displaying images designed to invoke a particular mood. The visual output may comprise multiple color components. This can further contribute to avoiding delirium, and provides significant benefits in this regard over and above a lighting assembly alone.

The visual output poses a problem however, in that it inevitably results in delivery to the patient of an additional melanopic luminous exposure, in addition to that administered by the lighting assembly. This means that any control program created for the lighting assembly and configured to administer a specific target melanopic luminous exposure will not result in that amount of light being delivered in total, since the additional visual output of the display means will result in a greater amount of light being delivered.

The invention hence in addition provides a solution to this in adjusting the originally specified target melanopic luminous exposure by an amount configured to compensate for the additional melanopic luminous exposure administered by the visual output. When the control schedule for the lighting assembly is executed simultaneously with display of the visual output, the melanopic luminous exposures of the two together combine to provide the original desired target melanopic luminous exposure.

The additional melanopic luminous exposure associated with the visual output (referred to above) means the additional melanopic luminous exposure delivered or administered by the visual output when displayed to a user.

The adjusted target melanopic luminous exposure may be determined by reducing the original target by an amount corresponding to the additional melanopic luminous exposure.

Melanopic luminous exposure is a term of the art and corresponds to a dosage of light delivered to a patient, equal to the product of the illuminance of the light and the time period over which it is delivered. It is typically measured in units of Lux Hours (Lux being the SI unit of illuminance). For brevity, in descriptions which follow, melanopic luminous exposure may be shorted simply to 'luminous exposure'. Unless stated otherwise, references to 'luminous exposure' should be read as referring to 'melanopic luminous exposure' as defined above.

According to one or more embodiments, the intended visual output of the visual display means may be associated with an array of constituting pixels. The further data input may in this case include information indicative of a luminous output of each pixel. The additional melanopic luminous output may be determined at least in part based on this further information. This provides an efficient approach to determining the additional luminous output.

This information may for instance be indicative of an illuminance level of each pixel. The illuminance level may correspond directly to the illuminance or may be indirectly representative of the illuminance, e.g. expressed in terms of a proportion of a maximum illuminance output.

The information indicative of luminous output may be indicative of a melanopic luminous output of each pixel. Melanopic luminous output means a luminous output of the pixel, weighted in accordance with its melanopic effect, meaning its biological effect upon the human circadian rhythm. It may be weighted for instance according to its color or color temperature, or each of a set of color components of the light output may be weighted according to their respective melanopic effect.

Melanopic luminous output may in particular mean a melanopic illuminance, meaning an illuminance of each pixel, weighted according to the melanopic effect of the light, for instance weighted according to the color or color temperature of the light.

Preferably, determining the additional melanopic luminous exposure comprises aggregating the luminous outputs of the array of pixels. This then allows a total luminous output associated with the full visual output to be determined.

The visual output is associated with the array of pixels in the sense that the visual output is constituted or formed by them; the light outputs of the pixels together form the visual output. The pixels may be pixels of a display screen in some examples. The pixels may alternatively be pixels of a visual output projected onto a display surface for example.

According to examples, the luminous output of each constituting pixel of the visual output may be taken to refer to the luminous output of an LED or other light source comprised by the visual display means and associated with the particular pixel of the visual output.

Determining the additional melanopic luminous exposure may be based at least partly on a known relative positioning of each of at least a subset of the pixels, relative to a given user positioning. The relative positioning may in some examples be determined by the controller based on input information concerning the absolute positions of the visual display means and the user.

The relative positioning may include at least a distance between the user and each of at least a subset of the pixels.

The melanopic effect of a luminous output decreases with distance (decreases approximately with the square of the distance). By melanopic effect is meant the biological effect of the light, in terms of its relative impact on the human circadian cycle. Hence by including relative positioning of the user and the pixels in the determination, a more accurate determination of the additional melanopic luminous effect of the visual output can be made.

The further data input may include information indicative of a color content of the intended visual output of the visual display means. In this case, determining the additional melanopic luminous exposure may comprise applying one or more melanopic weighting factors corresponding to a relative melanopic effect of different wavelengths of light. The melanopic weighting factors may then be applied to the different color components, to determine a melanopic luminous output associated with each color component.

The biological effect of the light, in terms of its relative impact on the human circadian cycle (known as "melanopic effect") is dependent upon the color (or wavelength) of the light. Accordingly, the inventors of the present invention have determined a set of melanopic weighting factors quantifying this relative biological effect of different wavelengths of light in a manner which can be readily utilized by a technical system in creating a light therapy schedule. Systems in accordance with this set of embodiments take advantage of these weighting or correction factors provide more accurate determinations of melanopic luminous exposure.

Information indicative of color content may be information indicative of a luminous output (e.g. illuminance) contribution of each of a set of light color components of the visual output.

The information indicative of color content may be information indicative of a luminous output contribution of each of a set of light wavelength components (or spectral components) of the visual output.

The melanopic weighting factors may correspond to different melanopic effects of different colors or wavelengths of light. The different weighting factors may in examples correspond to different color temperatures of light.

The melanopic weighting factors may be received or acquired from a local or remote memory or data store for example. The weighting factors in other examples may be pre-stored. The weighting factors may be received or acquired as a data input.

The lighting assembly may in some examples be adapted to generate a white light output. This then complements the color output of the visual display means.

In cases where the visual output is formed by pixels, the further data input may include information indicative of an illuminance level of each of a set of different light color components of a luminous output of each pixel.

The melanopic weighting factors described above may in this case be applied to the color components of each pixel, to determine a melanopic output associated with each color component. The color components may be aggregated for each pixel to determine a total melanopic luminous output for each pixel. The totals for each pixel may then be aggregated to give a color-weighted luminous output for the whole visual output.

The illuminance level may be illuminance itself, or may be information from which illuminance can be determined, e.g. a relative illuminance value representative of a proportion of a maximum possible illuminance of the given color component for the given pixel.

In examples, the color content of the visual output of each pixel's luminous output may include each of at least a red, green and blue color component. The determination of the additional melanopic luminous exposure may in this case be based on a simplified color content in which the red component is omitted.

Red light has almost negligible melanopic effect. Therefore, it may be discounted in determining the additional melanopic luminous exposure without having any substantial impact on the accuracy of the determination.

The visual output may be composed of RGB (red-green-blue) pixels.

In further examples, the determination of the additional melanopic luminous exposure may be based on a further simplified color content in which only the blue color component is considered or included. Blue has by far the largest melanopic effect of red green and blue light. Hence, just calculating the additional melanopic luminous exposure on the basis of the blue component greatly simplifies the calculation, without substantially reducing accuracy.

According to preferred embodiments, the lighting assembly and the visual display means may be integrated in a single unit. For example, the two may be integrated in a single display unit, e.g. a single panel, e.g. a single display panel or single lighting panel. The single unit may for instance comprise a first array of light sources (e.g. LEDs) corresponding to the lighting assembly and for creating the light output with controllable illuminance and a further array of light sources (e.g. LEDs) corresponding to the visual display means and for generating the visual output. The two arrays of light sources may for example be arranged adjacent to one another, or interleaved with one another, or with one inset inside the other, or may be mixed or integrated with one another.

In alternative examples, the lighting assembly and visual display means may be comprised by separate units, for instance separate panels.

According to one or more examples, the lighting assembly may be formed by or may comprise a plurality of lighting panels. In one or more examples, there may be provided a plurality of visual display means or the visual display means may comprise a plurality of display panels. The plural visual display means and/or lighting assemblies may be controlled in a coordinated manner to generate the circadian light output and the visual output respectively.

In examples, the visual output may comprise one or more images for presentation to the user.

In examples, the visual output may comprise one or more video images for presentation to the user, i.e. composed of a plurality of images frames.

In some embodiments, the visual output may comprise a video image composed of a plurality of image frames, and wherein determining the additional melanopic luminous exposure comprises determining a melanopic luminous output of each of the image frames and aggregating the determined image frame melanopic luminous outputs.

Melanopic luminous output means a luminous output of the pixel, weighted in accordance with its melanopic effect, meaning its biological effect upon the human circadian rhythm. It may be weighted for instance according to its color or color temperature, or each of a set of color components of the light output may be weighted according to their respective melanopic effect.

Melanopic luminous output may in particular be a melanopic illuminance, meaning an illuminance of each pixel, weighted according to the melanopic effect of the light, for instance weighted according to the color or color temperature of the light.

According to more particular examples, each image frame of the video image may be associated with an array of constituting pixels, and wherein the further data input includes information indicative of a luminous output of each of the pixels of each frame, and wherein determining the melanopic luminous output of each frame comprises for the given frame aggregating the luminous outputs of the array of pixels associated with the frame.

Luminous output here may be understood in the same way as described above.

In accordance with an advantageous subset of embodiments, the light output of the lighting assembly may further have a controllable color temperature. As the skilled person will recognize, color temperature is different to absolute color, and in general simply relates to different 'warmth' levels of generally white light, progressing from bluish white (over ~5000 Kelvin) to yellowish white to red (~2700-3000 Kelvin).

In particularly advantageous embodiments, the controller may be further adapted to retrieve from a data store one or more melanopic weighting factors corresponding to a relative melanopic effect of different color temperatures of light, and wherein the control schedule is created based on the melanopic weighting values and the adjusted target melanopic luminous exposure and is for controlling the illuminance and color temperature of the lighting assembly over time such as to deliver in total over the defined treatment period the adjusted target melanopic luminous exposure.

According to this subset of embodiments, the color temperature of the light generated by the lighting assembly is controllable, and furthermore the controller is configured to take into account the different melanopic effects of different light color temperatures when generating the control schedule. This hence provides an additional degree of controllability and flexibility, and intelligently adapts the delivery of light according to the melanopic weighting of the light color temperature composition.

It has recently been discovered that the biological effect of the light, in terms of its relative impact on the human circadian cycle (known as "melanopic effect") is dependent upon the color temperature of the light. Accordingly, the inventors of the present invention have determined a set of melanopic weighting factors quantifying this relative biological effect of different color temperatures of light in a manner which can be readily utilized by a technical system in creating a light therapy schedule. Accordingly, 'melanopic luminous exposure' may for the purposes of this subset of embodiments be understood as referring to the color temperature weighted melanopic luminous exposure (the melanopic luminous exposure in lux hours further adjusted for the relative melanopic or biological sensitivity of humans to light of different color temperatures).

The controller is adapted to retrieve the set of relative weighting factors from an associated data store and to accordingly set intensity and color temperature values of the light output within the control schedule such that throughout the duration of the treatment period, the adjusted target melanopic luminous exposure is delivered.

Creating a lighting schedule for reducing delirium in which melanopic effect of the color temperature of the light is taken into account represents a significant departure from known systems in the art. Not only is color temperature taken into account, the system includes a lighting assembly in which the color temperature is controllable. The controller is therefore able to configure color temperature as one of a plurality of variable parameters in the control schedule. In certain embodiments for instance, a user may specify a preferred color temperature, and a control schedule may then be determined such as to include light of that color while still ensuring delivery of the specific (adjusted) target melanopic luminous exposure.

In particular, the controller may be adapted to receive color temperature preference data indicating one or more preferred color temperature values, and to create the control schedule such that the color temperature of the light output, for at least a portion of the treatment period, has the preferred color temperature value.

Accordingly, these embodiments are able to provide efficient technical implementation of a light output therapy which delivers a required melanopic luminous exposure, while allowing a greater degree of configurability over color temperature, without impacting on the accuracy of the light dosage delivered. This offers greater choice to patients and users of the system who may prefer light of certain color temperatures, and also offers greater flexibility to clinicians in configuring the light treatment.

Examples in accordance with a further aspect of the invention provide a light therapy method comprising controlling a lighting assembly to deliver a determined melanopic luminous exposure, the lighting assembly being operable to create a light output having a controllable illuminance, and the method comprising:

receiving a data input indicating a target melanopic luminous exposure for administration by the lighting assembly;

receiving a further data input indicative of one or more luminous characteristics of a visual output intended for presentation by a visual display means;

determining, based on the further data input, an estimated additional melanopic luminous exposure associated with the intended visual output;

determining an adjusted target melanopic luminous exposure for administration by the lighting assembly, based on reducing the target melanopic luminous exposure so as to compensate for the additional melanopic luminous exposure;

creating, based on the adjusted target melanopic luminous exposure, a control schedule for controlling the illuminance of the lighting assembly over time such as to deliver in total over a defined treatment period the adjusted target melanopic luminous exposure; and controlling the lighting assembly in accordance with the control schedule.

In examples, the further data input may include information indicative of a color content of the intended visual output of the visual display means, and wherein determining the additional melanopic luminous exposure comprises applying one or more melanopic weighting factors corresponding to a relative melanopic effect of different wavelengths of light.

According to one or more examples, the intended visual output of the visual display means may be associated with an array of constituting pixels, and wherein the further data input includes information indicative of a luminous output of each pixel, and wherein the further data input includes information indicative of an illuminance level of each of a set of different light color components of a luminous output of each pixel.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
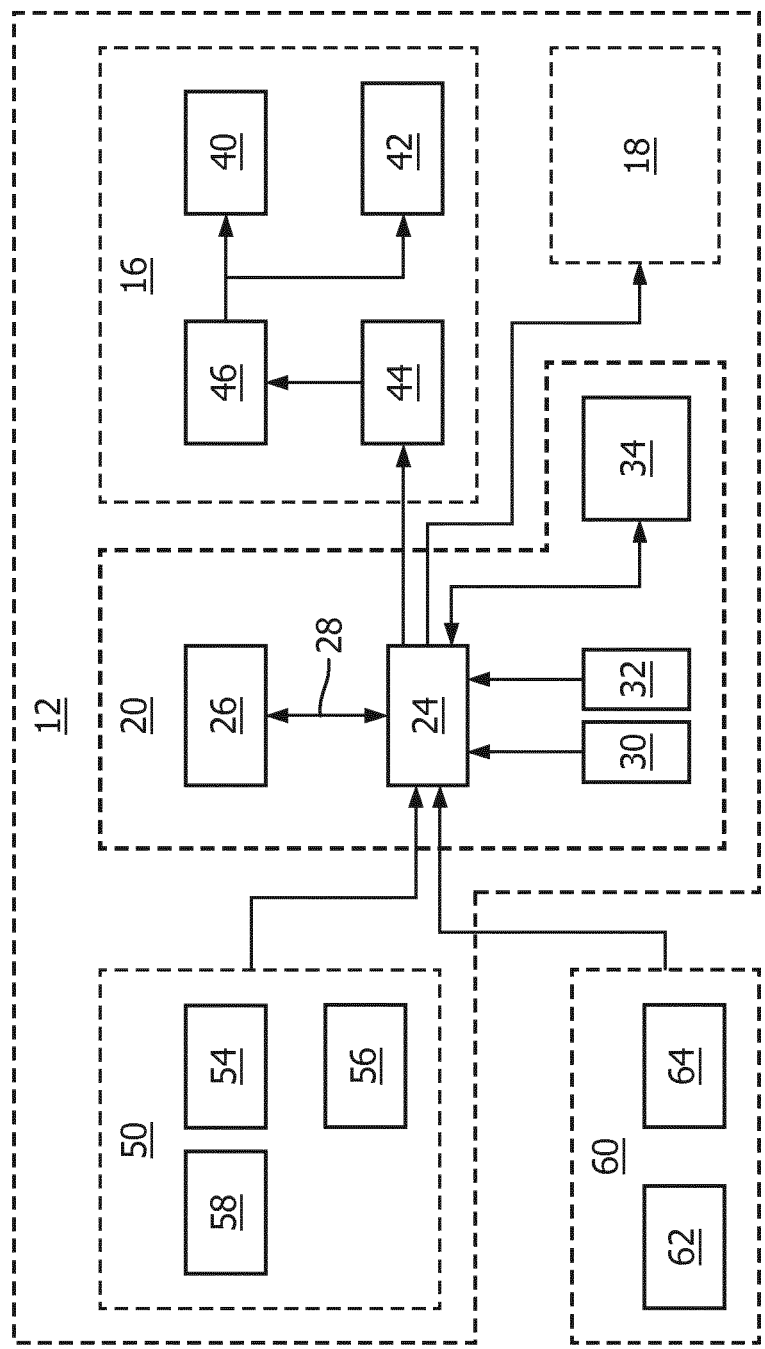
FIG. 1 is a block diagram showing an example light therapy system in accordance with an embodiment of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a light therapy system for administering a controllable melanopic luminous exposure. The system includes a controllable lighting assembly for delivering the melanopic luminous exposure to the patient. The system further includes a visual display means for presenting a visual output such as a video to the patient. A target melanopic luminous exposure for administration to the patient is received. This is then adjusted to compensate for an additional melanopic luminous exposure which the visual display means generates in displaying the visual output. A control schedule is then generated for controlling an illuminance of the lighting assembly so as to deliver over a defined treatment period the adjusted target melanopic luminous exposure. The lighting assembly is then controlled according to the control schedule. In this way both the visual output of the visual display means and the light output of the lighting assembly can be administered, while ensuring that the original target melanopic luminous exposure is delivered, and is not exceeded.

A preferred embodiment of the invention will now be described in detail with reference to FIGS. 1 and 2.

Lighting systems in patient rooms are often designed more around the functionality of the light for caregivers than the clinical effect of the light upon (in particular the circadian rhythm of) patients. The present invention aims to redress this problem.

The system of the present invention allows clinicians to specify a desired melanopic luminous exposure to be administered to a given patient, with the system configured to ensure that the patient receives the prescribed dosage of light. To this end, in accordance with a preferred set of embodiments, the system at first calculates, based on the clinician's prescription and the characteristics of the used lighting assembly, a tailored light therapy schedule or program specifying the required timing, illuminance and color temperature of the light across a defined treatment period. The controller then executes the light therapy by controlling the lighting assembly in such a way that it delivers the light as specified in the schedule.

In certain examples, feedback sensors may in addition be provided and the light therapy program adjusted in accordance with a closed loop configuration based on the amount of detected ambient daylight, detected patient presence or absence, and/or the duration for which a patient's eyes are open or closed.

FIG. 1 shows a block diagram of an example light therapy system 12 in accordance with an embodiment of the invention. FIG. 2 schematically depicts an example physical layout of the example system 12.

The system comprises a lighting assembly 16 operable to create a light output having a controllable illuminance and color temperature. The system further comprises a visual display means 18 for creating a visual output. In the illustrated example, the lighting assembly and visual display means are integrated in a single lighting panel 48 (as shown in FIG. 2). In particular, the lighting assembly 16 comprises a first array of LEDs and the visual display means comprises a second array of LEDs, the second array of LEDs being RGB LEDs for creating a color output.

For brevity, in descriptions which follow, the visual display means 18 may be referred to simply as the display. The two terms may be understood as synonymous.

The lighting assembly 16 is operatively coupled to a controller 24 of a light therapy control unit 20. The light therapy control unit further comprises a user interface 26 and a first data store 30, a second data store 32 and a third data store 34. These elements are not essential as will be explained below.

The first data store 30 stores configuration and specification data relating to the lighting assembly 16, the second data store stores a set of melanopic weighting factors corresponding to the relative biological effect of different color temperatures of light, and the third data store comprises a set of one or more control schedule templates based upon which the controller 24 may create each control schedule. Although three data stores 30, 32, 34 are provided in the example of FIG. 1, in further examples these may for instance be combined into one data store and/or may be integrally comprised by the controller 24 or may be remote to the lighting system and communicatively linked to the controller 24.

The visual display means 18 of the lighting panel 48 comprises an array of display pixels (not visible) for generating visual images, and the screen or display surface of the display means is operable to display video images composed of multiple image frames. The display means 18 comprises an array of RGB LEDs, each operable to generate a light output having a red, green and blue light color component. Each RGB LED corresponds to a single RGB pixel having an associated light output having a red, green and blue light color component. The visual display means is thus operable to provide an RGB visual output, i.e. a visual output having a red, green and blue color component.

Control of RGB LEDs of the visual display means 18 may be in accordance with any suitable addressing protocol including by way of example the Digital Addressable Lighting Interface (DALI) protocol. This may be performed by the controller 24 or by a separate visual output display driver for example.

Figure 2:
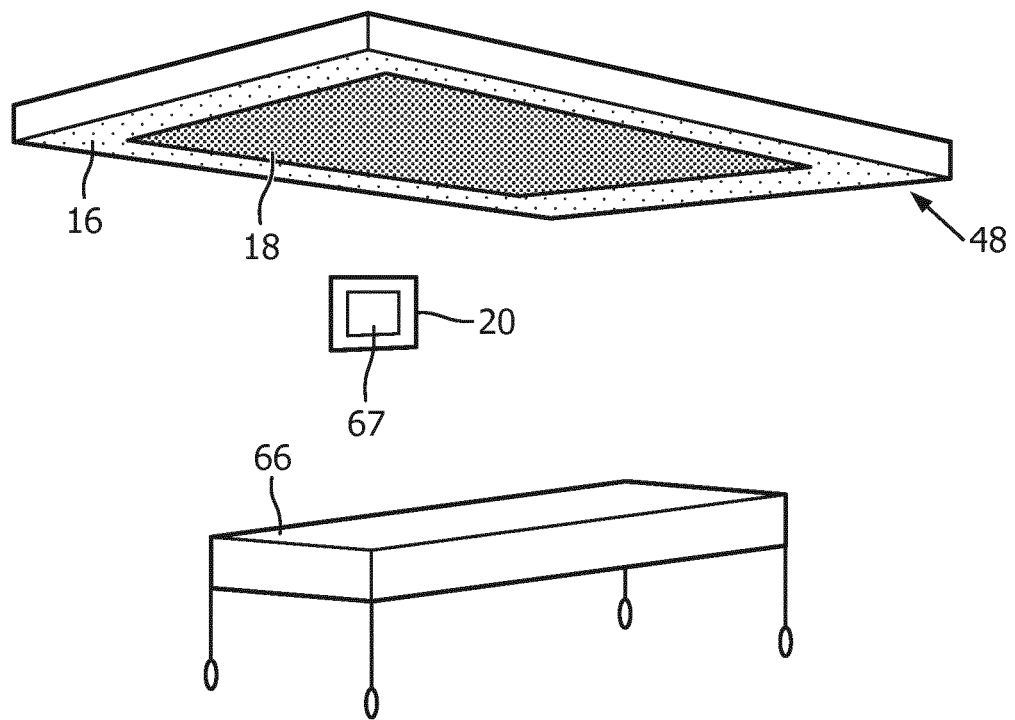
FIG. 2 schematically depicts the configuration in use of an example light therapy system according to an embodiment of the invention.
Figure 3:
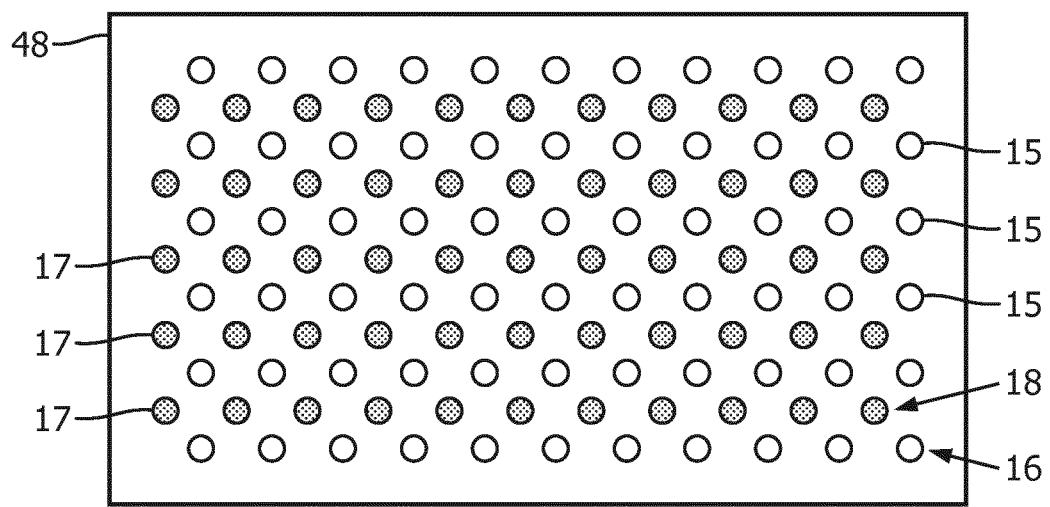
FIG. 3 schematically depicts an example configuration of a lighting assembly and visual display means as integrated in a single lighting panel.

The lighting panel 48 is shown in perspective view in FIG. 2, arranged above a treatment bed 66 in which a patient might lay or sit. The lighting panel may thus form a ceiling panel. In use, the visual display means part 18 generates the visual output and presents it toward the bed for viewing by the patient. The visual output is preferably a video image output, e.g. a series or playlist of videos. The lighting assembly 16 part of the lighting panel 48 is (in this example) arranged surrounding the visual display means. The lighting assembly comprises a further array of LEDs, having a controllable illuminance. The lighting assembly LEDs may be white LEDs. They may have a controllable color temperature.

In use, the controller 24 of the control unit 20 is adapted to receive from the user interface 26 a data input 28 indicating a target melanopic luminous exposure for administration by the lighting assembly 16. The controller is further adapted to receive a further data input indicative of one or more luminous characteristics of a visual output intended for presentation by the visual display means 18. In particular, in the present example, the further data input includes information indicative of an illuminance level of each of the red green and blue color components of the luminous output of each RGB LED or pixel. More particularly, in one preferred set of embodiments, the further data input is representative of luminous characteristics in the form of RGB DALI values for each RGB LED comprised by the visual display means 18. The RGB DALI values correspond to illuminance levels of each of a red, green and blue LED element of each RGB LED.

The further data input may for example be received from the visual display means 18 itself, or from a driver comprised by the display means (not shown) or from an external display controller for controlling the display means to present the visual output for example.

The controller 24 is further adapted to determine, based on the further data input an estimated additional melanopic luminous exposure associated with the intended visual output of the display 48. A process for determining this will be described in greater detail below.

The controller 24 is subsequently adapted to determine an adjusted target melanopic luminous exposure for administration by the lighting assembly 16, based on reducing the target melanopic luminous exposure so as to compensate for the additional melanopic luminous exposure. The original target melanopic luminous exposure received from the user interface 26 may be reduced by an amount corresponding to the additional melanopic luminous exposure for example. This will be described in greater detail below.

The controller 24 is preferably adapted to retrieve from one of the data stores (for the purposes of the present example this is assumed to be the second data store 32) a set of melanopic weighting factors corresponding to different biological sensitivities of the body to various color temperatures of light. Based upon these factors (as well as possibly other factors) the controller is adapted to create a control schedule for controlling illuminance and preferably also color temperature values of the lighting assembly 16 over time such as to deliver in total over the course of a defined treatment period the adjusted target melanopic luminous exposure. The controller is then configured to execute this control schedule by means of suitable communication with the lighting assembly 16.

The lighting assembly 16 for the present example is assumed to comprise two sets of LED modules 40, 42, each, in use, emitting light of a different spectral composition, and of a different color temperature. The first set of LED modules 40 is adapted to emit light of a cool color temperature (corresponding broadly to light of temperature greater than 5000 Kelvin) and the second set of LED modules 42 is adapted to emit light of a warm color temperature (corresponding broadly to light having a temperature in the range of approximately 2700-3000 K).

When the two sets of LED modules 40, 42 are activated simultaneously, a combined light output is generated, formed of a mix of light from each set. By appropriately controlling the relative light levels (i.e. power output) of each of the two sets of modules, light of a broad range of different color temperatures can be generated. For instance, by emitting the cold LED modules at greater relative power, a relatively cold light output may be created; emitting the warm LED modules at greater relative power will generate light of warmer relative color temperature.

The lighting assembly 16 further comprises a local light assembly controller 46 for controlling the relative light levels of the LED modules 40, 42 such as to create a light output of a given color temperature and a given illuminance. Control by the driver may be in accordance with any suitable addressing protocol including by way of example the Digital Addressable Lighting Interface (DALI) protocol.

In use, once the controller 26 has generated a control schedule suitable for delivering the adjusted target melanopic luminous exposure, the controller 26 communicates with the lighting assembly controller 46 to instruct it to control the LED modules 40, 42 so as to generate at appropriate times light outputs being in accordance with the created schedule.

Although LED modules are used in particular in the present example, this is not essential to the invention. Other lighting assemblies may be used, for instance comprising other forms of solid state light sources, or alternatively fluorescent or incandescent light sources for instance. Two sets of light modules 40, 42 are provided in the example of FIG. 1. However, this is again not essential. In further examples, a greater or lesser number may be provided. A single lighting module may be provided operable to generate a combined light output of a configurable color temperature and illuminance.

Although in the present described embodiment, the lighting assembly 16 has a controllable color temperature, this is not essential to the invention. The lighting assembly may in further examples be adapted to generate light of only a single color temperature, e.g. a single shade or color of white or variant of white (such as off-white). The general concept of the invention, with regards to the lighting assembly, only requires that the lighting assembly is operable to create a light output having a controllable illuminance. Any configuration or technical implementation of this concept will be suitable. In advantageous embodiments, such as the ones shown in FIGS. 1-4 and described in detail above and below, the lighting assembly also has a controllable color temperature.

Where the lighting assembly does not have a controllable color temperature, the lighting assembly may for example comprise only a single light module for generating the single of color temperature of light.

Furthermore, where the lighting assembly 16 does not have a controllable color temperature, the controller 24 is adapted to generate a control schedule for controlling illuminance of the lighting assembly over time, but not color temperature. The control schedule is configured to deliver in total over the course of a defined treatment period the adjusted target melanopic luminous exposure. The controller is not required in this case to retrieve the melanopic weighting factors corresponding to different color temperatures of light.

Although in the particular example of FIGS. 1 and 2, the lighting assembly 16 comprises a local light assembly driver for controlling light output, alternatively this function may be performed by the controller 24 of the light therapy system.

Additionally, although the control unit 20 in the present example comprises first 30, second 32 and third 34 data stores, it will be recognized by the skilled person that inclusion of these components is not essential to the invention, but pertains to the particular detailed embodiment of FIG. 1. In further examples, data concerning the lighting assembly 16 may be stored elsewhere, e.g. locally at the lighting assembly. In further examples, template control schedules may not be used in generating the control schedule, and so a data store for these templates is not needed, or templates may be retrieved from data stores elsewhere. In the case that the lighting assembly does not have a controllable color temperature, a data store for storing melanopic weighting factors for different color temperatures is also not needed for instance.

The user interface 26 is also not essential. The target melanopic luminous exposure may be received or acquired from a different source, e.g. a remote user input such as from a mobile device operating an app or from a data store or memory.

Optionally, the system further includes an assembly 50 of sensors 54, 56, 58 for providing feedback in adjusting parameters of the light therapy schedule such as to ensure delivery of a target melanopic luminous exposure. This optional feature will be described in greater detail below.

Optionally also, the system may be communicatively coupled with a patient data management system 60 comprising a medical record system 62 and a patient monitoring system 64. This may enable integration of the delivered light therapy with broader clinical targets and objectives for the patient as well as enabling in some examples adaptation of the therapy in accordance with certain patient-specific clinical parameters or needs (such as age or cumulative duration of stay). This optional aspect will also be described in greater detail in sections to follow.

In the illustrated example of FIG. 2, the lighting assembly 16 and the visual display means 18 are integrated in a single lighting panel 48, with the lighting assembly comprising one array of LEDs and the visual display means comprising a second array of LEDs, and wherein the lighting assembly array is distinct from, and arranged surrounding, the visual display means array. However, this is by way of illustration only, and in other examples, the relative configuration or arrangement of the visual display means and lighting assembly may vary.

According to one set of examples for instance, the visual display means 18 and lighting assembly 16 are integrated in a single panel, but wherein the two are interleaved with one another, to form a single light output area comprising LEDs belonging to both. This arrangement is illustrated schematically in FIG. 3 which depicts a light output area of a lighting panel 48 and the arrangement of LEDs comprised by the panel. The panel comprises a first array of LEDs 15 forming the lighting assembly 16 and a second array of LEDs 17, interleaved or interwoven with the first, forming the visual display means 18. The LEDs of the visual display means are RGB LEDs. A single light output area is thus formed, composed of the LEDs of both the lighting assembly 16 and the visual display means 18.

Figure 4:
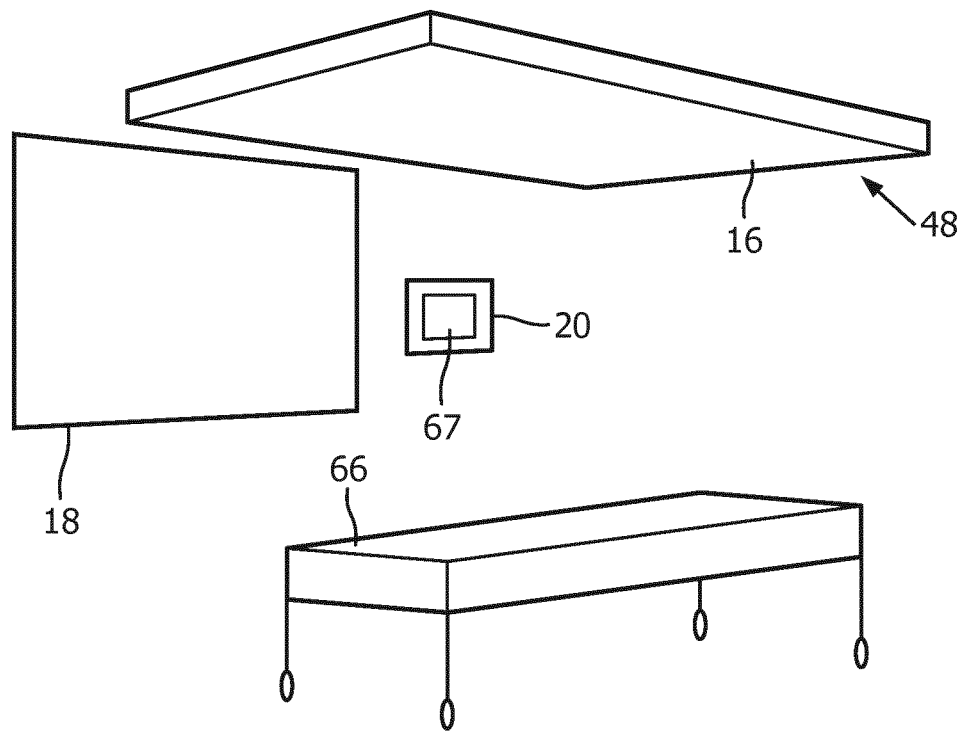
FIG. 4 schematically depicts a further example configuration of an example light therapy system according to an embodiment.

Furthermore, although in the above examples, the lighting assembly 16 and visual display means 18 are integrated in a single display panel 48, in further examples, each may form a separate unit. An example is schematically depicted in FIG. 4, which shows a physical set up of a further example light therapy system. The system comprises a ceiling panel 48 which comprises or houses the lighting assembly 16, and further comprises a separate (wall) panel which comprises or houses the visual display means.

The lighting assembly 16 for the purposes of this example is assumed to be an LED-based lighting panel 16. The lighting assembly panel is shown arranged above a treatment bed 66 in which a patient might lay or sit. In use, the light panel 16 emits a light output toward the bed for delivery to a patient.

It is preferred that the ceiling panel comprises the lighting assembly 16 for administering the primary light output of the light therapy. However, in other examples the wall panel may comprise the lighting assembly and the ceiling panel 48 may comprise the visual display means 18.

The lighting assembly and visual display means may otherwise take the same form as described in the above examples. In particular, each comprises an array of LEDs, with the lighting assembly for instance comprising an array of white LEDs optionally having a controllable color temperature, and the visual display means comprising an array of RGB LEDs.

According to further examples, the lighting assembly 16 may comprise or be formed by a plurality of separate lighting panels. According to one or more examples, the visual display means may comprise or be formed by a plurality of display panels.

In accordance with all embodiments of the invention, the control schedule is generated on the basis of an adjusted target melanopic luminous exposure. The adjusted target melanopic luminous exposure is determined based on the original target melanopic luminous exposure and an estimated further melanopic luminous exposure associated with the visual output of the visual display means 48.

An example procedure for determining an estimated additional melanopic luminous exposure will now be described. For brevity, in descriptions which follow, the visual display means 18 may be referred to simply as the display. The two terms may be understood to be synonymous.

A still image for presentation by the visual display means 18 is assumed to consist of n×m pixels. Each pixel has a certain light output color content, which can be represented as an RGB triplet (r, g, b) indicating a respective magnitude of each of a red, green, and blue color component in the pixel light output. If, for example, the component values can vary within the range from 0 to 255, then (0, 0, 0) represents black and (255, 255, 255) represents the brightest representable white.

As noted above, the visual display means 18 of each of the example light therapy systems 12 outlined above comprises an array of RGB LEDs, each LED corresponding to a single pixel of each still image (frame) generated by the display.

By way of example, the visual display means 18 is assumed to comprise n×m RGB LEDs. The LEDs may be controlled in accordance with any suitable addressing protocol including by way of example the Digital Addressable Lighting Interface (DALI) protocol. Either the controller 24 or a separate, e.g. local, display driver or controller is adapted in use to render a given still image by using the RGB values of each pixel of the image to be rendered as DALI values for driving the RGB LEDs at the corresponding pixel position on the display 18. The RBG values of each pixel may be received or acquired or generated by the controller or separate driver for instance from an further external controller or data store for example, or the pixel RGB values may be stored locally.

The LED DALI values correspond to a respective illuminance level of the red, green and blue LED elements of each RBG LED. An LED DALI value of (0, 0, 0) corresponds to no light output from the RGB LED, i.e. the red, green, and blue LED elements are switched off. An LED DALI value of (255, 255, 255) corresponds to the red, green, and blue LED elements illuminated with highest intensity, resulting in the brightest white light.

For the purposes of the present example, $E_R$ will denote a maximum illuminance output at the eye level of a user of a red LED element of a given RGB LED, i.e. (255, 0, 0). $E_G$ denotes a maximum illuminance output at the eye level of patient of the green LED element of a given RGB LED, i.e. (0, 255, 0). $E_B$ denotes a maximum illuminance output at the eye level of patient of the blue LED element of a given RBG LED, i.e. (0, 0, 255).

Since the melanopic effect of light depends on the wavelength, correction factors $c_R$, $c_G$, $c_B$ are preferably utilized for calculating a corresponding maximum melanopic illuminance of each of the red, green, and blue LED elements of each RBG LED:

$$E_{R,mel}=c_R*E_R$$

$$E_{G,mel}=c_G*E_G$$

$$E_{B,mel}=c_B*E_B$$

The melanopic illuminance at the eye level of a user of an RGB LED driven with a DALI triplet of (r, g, b) is then given by:

$$E_{RGB,mel}(r,\ g,\ b)=[(E_{R,mel}*r+E_{G,mel}*g+E_{B,mel}*b)/255]$$
lux

By way of a specific example, if an RGB LED comprises a red LED with a light output having central wavelength at 640 nm, a green LED with central wavelength at 560 nm and a blue LED with central wavelength at 440 nm, then the correction factors are as follows:

$$c_R=0.00147$$

$$c_G=0.29103$$

$$c_B=15.03135$$

By way of further examples, the correction factor for a blue LED of central wavelength 460 nm is $C_B=10.72935$. The correction factor for a blue LED of central wavelength 495 nm (cyan) is $C_B=3.11931$. The correction factor for a yellow LED of central wavelength 585 nm is 0.03935. The correction factor for a yellow LED of central wavelength 615 nm (amber) is 0.00506.

Further correction factors for light outputs of other central wavelengths can be derived using the following documents and standards: German standard DIN SPEC 5031-100:2015, and the scientific paper "Measuring and using light in the melanopsin age" by Lucas et al. (2014) Trends Neurosci, 37(1), 1-9.

These correction factors are reflective of the fact that red light has almost negligible melanopic effect, green light a small melanopic effect, and blue light a very large melanopic effect (where melanopic effect means the biological effect of the light, in terms of its relative impact on the human circadian cycle).

If the maximum illuminance for the red, green, and blue LED is 1 lux, i.e. $E_R=E_G=E_B=1$ lux, then a pixel with RGB color triplet (150, 200, 100) rendered by such an RGB LED generates a melanopic illuminance of $$E_{RGB,mel}(150, 200, 100)=(0.00147*1\ lux*150+\\0.29103*1\ lux*200+15.03135*1\ lux*100)/255\\melanopic\ lux=6.124\ melanopic\ lux$$

To calculate the melanopic illuminance of a still image having n×m pixels, the melanopic illuminances for all pixels are calculated, and summed (aggregated). This procedure may be represented for instance by the following algorithm (expressed in the form of pseudo C computer code):

```
Melanopic_Illuminance := 0;
i := 0; j := 0;
while (i +21 n)
    while (j < m)
        RGB := RGB (i , j);
        r := Red(RGB); g := Green(RGB); b := Blue(RGB);
        Melanopic_Illuminance += (E_{R,mel} * r + E_{G,mel} * g +
        E_{B,mel} * b) / 255;
        j++;
    i++;
```

The algorithm initially sets the (total) melanopic_illuminance variable at zero. Then, index variables i and j are defined for indexing through the rows and columns, and these are set at zero. Then, indexing through each element of each row (i), and column (j), the RGB DALI values of the RGB LED corresponding to that element are retrieved. These may be retrieved for example from the display 18 itself or a driver or controller comprised by the display, or from a data store or memory for example.

Then, the r, g, b values of the (r, g, b) triplet of the image pixel to which the respective RGB LED corresponds are set to be equal to the corresponding red, green, and blue DALI values. The melanopic illuminance for the pixel is then calculated in the manner described above, and the total melanopic illuminance variable then incremented (+=) by the value of the pixel melanopic illuminance.

A corresponding (additional) melanopic luminous exposure contributed by the presentation of the image is given by the product of the melanopic illuminance of the image and time for which it is displayed.

In advantageous examples, the visual display means 18 is utilized for displaying a visual output in the form of a video image comprising a plurality of image frames displayed in sequence.

There will now be described an example procedure for determining an (additional) melanopic luminous exposure associated with display of a video image.

For calculating the melanopic luminous exposure (i.e. melanopic illuminance×time duration) of a video consisting of a sequence of p still images shown one after the other, each for q seconds (i.e. a video displayed at 1/q frames per second), the melanopic exposure for all of the individual still images is calculated and summed (aggregated).

This procedure may be represented for instance by the following algorithm (expressed in the form of computer code):

```
Melanopic_Exposure := 0;
k := 0;
while (k < p)
    Melanopic_Exposure += Melanopic_
    Illuminance(k) * q;
    k++;
```

Here, the algorithm initially sets the (total) melanopic_exposure variable (for the whole video) at zero. Then, an indexing variable k is defined for indexing though the frames of the video, and initially set at zero. Then, for each frame k, up to the final frame p, total melanopic luminous exposure is incremented by a respective product of the melanopic illuminance for that frame and the time duration q of the frame (in seconds or hours).

The melanopic illuminance of each frame, Melanopic_Illuminance(k) may be calculated for each frame as described in preceding the algorithm above. This may be performed concurrently with execution of the melanopic exposure algorithm above (i.e. the melanopic illuminance for each frame is calculated immediately before incrementing the melanopic exposure by that value), or all of the melanopic illuminance values may be determined in advance in a separate algorithmic process.

In certain advantageous embodiments, the visual display means 18 may be controlled to display a video playlist, i.e. a series of video images displayed in sequence. There will now be described an example procedure for determining an (additional) melanopic luminous exposure associated with display of a video image playlist.

To calculate the total melanopic exposure of a video playlist which consists of a sequence of v videos shown one after the other, the melanopic luminous exposure for each video of the playlist is determined and summed (aggregated).

This procedure may be represented for instance by the following algorithm (expressed in the form of computer code):

```
Total_Melanopic_Exposure := 0;
u := 0;
while (u < v)
    Total_Melanopic_Exposure += Melanopic_
    Exposure(u);
    u++;
```

Here, the algorithm initially defines and sets the Total_Melanopic_Exposure variable (for the whole video playlist) at zero. Then, an indexing variable u is defined for indexing though the individual videos of the playlist, and initially set at zero. Then, for each video u, up to the final video v, total melanopic luminous exposure is incremented by the value of the melanopic exposure for that video.

The melanopic luminous exposure of each video, Melanopic_Illuminance(u) may be calculated for each video as described in preceding the algorithm above. This may be performed in tandem with execution of the melanopic exposure algorithm above (i.e. the melanopic exposure for each video is calculated immediately before incrementing the total playlist melanopic exposure by that value), or all of the melanopic exposure values may be determined in advance in a separate algorithmic process.

The above paragraphs have described example procedures for determining the additional melanopic luminous exposure associated with example visual outputs to be displayed by a visual display means 18.

Following this, it is necessary to determine an adjusted target melanopic luminous exposure for administration to the user, the adjusted target being reduced in compensation for the additional melanopic luminous exposure.

By way of example, a physician may prescribe for a given patient a certain total melanopic luminous exposure TMLE_Patient and a particular video playlist for display to the patient. The controller 24 of the light therapy system 12 then first calculates the total (additional) melanopic luminous exposure of the given video playlist TMLE_VideoPlayList as described above. This includes receiving a data input representative of luminous characteristics of the video playlist, preferably in the form of DALI RGB light values for each RGB LED constituting the visual display means 18 for each frame of each video. As described above, from this, a melanopic luminous exposure for each video, and the video playlist, can be determined.

The adjusted target melanopic luminous exposure may then be calculated. In a simple case, this may be determined as

[Adjusted Target Melanopic Luminous Exposure]=
[Original Target Melanopic Luminous Exposure]−[Additional Melanopic Luminous Exposure]

i.e.

Adjusted Target Melanopic Luminous Exposure=TMLE_Patient−TMLE_VideoPlayList

Based on this calculation, a control schedule is generated by the controller 24 for controlling at least the illuminance of the lighting assembly 16 (and optionally also the color temperature) over time such as to deliver in total over a defined treatment period the adjusted target melanopic luminous exposure.

The lighting assembly 16 is then controlled by the controller 24 or a driver of the lighting assembly or the lighting panel 48 in accordance with the control schedule, to deliver the adjusted target melanopic luminous exposure. Simultaneously, the visual display means 18 is controlled to present the visual output, i.e. the video playlist according to the example above. The visual output and the light output of the lighting assembly together administer to the patient the originally defined target melanopic luminous exposure.

A number of further optional features and variations pertaining to the calculation of the additional melanopic luminous exposure of the visual display means 18 will now be described.

The calculation (described above) of the melanopic luminous exposure associated with a given video for display by the display means 18 may preferably be performed only once, and the result for instance stored for any future use of the video. This avoids the need to recalculate the melanopic luminous exposure each and every time the video is to be played.

For example, the calculation may be performed once whenever a new video is added to a video database. A video database and corresponding melanopic luminous exposure values may be stored locally at the system 12 in a data store for instance. A dedicated data store may be provided for this. Alternatively, a video database and corresponding melanopic luminous exposure values may be stored remotely to the system and retrieved through a suitable communication link.

According to one or more embodiments, the calculation of the melanopic illuminance of a given RGB pixel may be simplified by ignoring or discounting the red light output component of a pixel since the color red has almost negligible melanopic effect (as noted above). Hence the calculation may simply not include or take account of the red (r, g, b) triplet value or the red RGB LED DALI value.

The calculation may in further examples be simplified even further by only taking into account the blue light output component of a pixel, since blue contributes by far the greatest melanopic effect. Here, the calculation of melanopic illuminance may simply not include or take account of the red or green (r, g, b) pixel triplet value or the red or green RGB LED DALI value.

The additional melanopic luminous exposure and adjusted target melanopic luminous exposure may be calculated at various times during the control procedure. Both of these values may in some examples be calculated in advance of determining and executing the control schedule for controlling the lighting assembly 16. Alternative, these may be calculated in real time as the light therapy is executed.

For example, instead of calculating the additional melanopic luminous exposure of the desired playlist and the corresponding adjusted target luminous exposure before the light therapy begins, the calculation can also be done while the light therapy is being delivered. For example, the additional melanopic luminous exposure can be straightforwardly estimated by summing up only the red DALI values at the level of the driver level and multiplying this by the elapsed therapy duration and the known melanopic color correction factor while the video playlist is rendering. Once the original prescribed melanopic luminous exposure is reached, the white light LEDs can be switched off.

According to one or more embodiments, the calculation of the melanopic illuminance may be performed in a more accurate way by taking the position of a pixel in an image-to-be-displayed into account. For example, the distance between a given pixel and the eye of a patient may be calculated. Since the melanopic effect decreases approximately with the square of the distance, the melanopic illuminance of a pixel depends not only on the RGB values but also on the distance to the eye.

The distance can be calculated by using an assumed position of a patient and a known position of the visual display means 18. For example, considering FIG. 2, the patient might be assumed to have their head located at a particular one of the ends of the treatment bed 66, with their eyes a certain distance from the bed surface. From this, if the position of the visual display means 18 part of the lighting panel 48 relative to the bed is known, and the position of a given pixel LED within the display is known, a distance of each pixel or LED to a patient's eyes(s) can be estimated or determined.

According to one or more examples, the calculation of the melanopic luminous exposure of a visual output of the visual display means 18 may additionally be used to check whether it is below a certain defined threshold for avoiding disturbance (e.g. waking up) of the patient. For example, it may be preferably that videos mimicking the sunrise or sunset should not deliver too high a melanopic luminous exposure.

If it the melanopic luminous exposure is detected as being above the defined threshold, the illuminance levels of the RGB pixels of the video may for example be reduced until the melanopic luminous exposure is below is the threshold.

In addition to the light therapy system 12, also other systems and devices in a patient room (e.g., a patient monitor) may contribute an additional melanopic luminous exposure administered to the patient, e.g. where devices comprise a screen or display which generates a light output. According to one or more examples, this additional luminous exposure may be taken into account in calculating the adjusted target melanopic luminous exposure. For example a melanopic luminous exposure generated by the luminous output of each further device may be calculated in a similar manner to the procedure described above for the visual display means 18. This may then be added to the additional melanopic luminous exposure calculated for the visual display means, and target melanopic luminous exposure reduced to compensate for the summed total additional luminous exposure.

Detailed procedures and options for generating the control schedule and for controlling the lighting assembly 16 to generate the required light output for implementing the control schedule will now be described.

To facilitate effective control of the lighting assembly and efficient generation of control schedules, various data sets may be stored in each of the first 30, second 32, and third 34 data stores of the control unit 20, associated respectively with the lighting assembly, the melanopic weighting of different color temperatures of light, and templates for generating control schedules.

It is to be understood that features pertaining to generating and controlling generation of lighting assembly light output of different color temperatures may be omitted in embodiments in which the lighting assembly does not have a controllable color temperature.

The first data store 30 preferably stores two primary data sets associated with the lighting assembly 16. Firstly, the data store 30 stores a table (or other suitable data structure) listing for all possible combinations of light levels (for instance DALI light levels) of the LED modules 40, 42, and the resulting color temperature of the light generated by the lighting assembly.

Table 1 below shows (an extract of) an example such color temperature table for a lighting assembly such as in FIG. 1 having a set of warm LED modules 42 and a set of cold (white) LED modules 40. It shows that if for example the cold white LED modules are powered at a (DALI) light level of 190 and the warm white LED modules at a (DALI) light level of 65, then the resulting color temperature is 5000 Kelvin.

TABLE 1

| DALI Light level | | Color |
|---|---|---|
| Cold LED Modules | Warm LED Modules | Temperature (Kelvin) |
| 0 | 255 | 2602 |
| 1 | 254 | 2635 |
| 2 | 253 | 2670 |
| ... | ... | ... |
| 122 | 123 | 4002 |
| ... | ... | ... |
| 190 | 65 | 5000 |
| ... | ... | ... |
| 255 | 0 | 6501 |

This data set may be used by the controller 24 to provide appropriate control instructions to the lighting assembly 16 to enable generation of light outputs of particular color temperatures.

A data set such as that of Table 1 may be generated empirically for a given lighting assembly 16, by varying the light level settings of the different LED modules 40, 42 and measuring the resultant color temperature of the combined light output. This could be implemented technically to speed up data collection, for instance by providing a controller configured to sweep rapidly through all possible combinations of light level settings and to measure the corresponding light output color temperature.

Alternatively, in some cases, a lighting assembly 16 may be provided with such a data set by the manufacturer.

Further to the color temperature table, the first data store 30 preferably also stores a table (or other data structure) listing the maximum and minimum possible illuminances the lighting assembly 16. This will generally be a function of the maximum and minimum illuminances of each of the component lighting modules 40, 42. This table may, among other things, be used by the controller 24 to ensure that control instructions provided to the lighting assembly 16 are not outside of its operational parameters.

Table 2 shows an example of such an illuminance data table. In this example for instance, the table indicates that the maximum illuminance of the relevant lighting assembly 16 is 2000 Lux (and the minimum 0). Preferably, illuminance in this table indicates illuminance as measured at the location of the patient and even more preferably at the location of the patient's eye(s).

TABLE 2

| Parameter | Min | Max |
|---|---|---|
| Illuminance LED Modules [Lux] | 0 (DALI = 0) | 2000 (DALI = 255) |

To improve accuracy of the delivered light therapy however, preferably the data set is generated empirically in situ, since the observed color temperature may depend upon the environmental conditions in which the light therapy system is operated. Measuring the resultant color temperature for each set of light levels should preferably be done as close as possible to the likely or actual position of the patient.

Preferably, the light therapy system 12 is configured to support a range of different specific lighting assemblies. To this end, the first data store 30 preferably contains configuration data (including one of each of the above data sets) for each supported lighting assembly. At installation time, data corresponding to the correct lighting assembly may be selected by the controller (or a user), either based on automated detection by the controller 24 of the connected lighting assembly, or based on user input provided via the user interface 26.

As discussed above, the biological effect of light upon the circadian rhythm of a patient depends upon the color temperature of the light. The controller 24 according to an advantageous set of embodiments may be configured to take account of these differing effects when creating a control schedule. To facilitate this, the second data store 32 may store a set of melanopic weighting factors for each possible color temperature of light. In some examples, a dedicated table may be provided for each lighting assembly 16 compatible with the system, listing weighting factors for only those color temperatures that the lighting assembly is able to generate. In other examples, a single comprehensive list may be provided listing weighting factors corresponding to every possible color temperature (or at least a comprehensive range). This list might be consulted for any lighting assembly.

Table 3 below shows an extract of an example set of weighting factors. The higher the factor, the higher the biological effect. Table 3 shows for example that the melanopic factor is 0.903 if the lighting assembly is operated at a color temperature of 5000 Kelvin.

TABLE 3

| Color Temperature (Kelvin) | Melanopic Weighting Factor |
| --- | --- |
| 2602 | 0.456 |
| 2635 | 0.461 |
| 2670 | 0.469 |
| ... | ... |
| 4002 | 0.780 |
| ... | ... |
| 5000 | 0.903 |
| ... | ... |
| 6501 | 1.035 |

Approximate values for melanopic weighting factors corresponding to color temperatures falling in between the values recited in the table may be derived by linear interpolation between neighboring data points in the table. For example, to derive an approximate weighting factor for a color temperature of 3000 K, linear interpolation may be applied between 2670 K and 4002 K.

Figure 5:
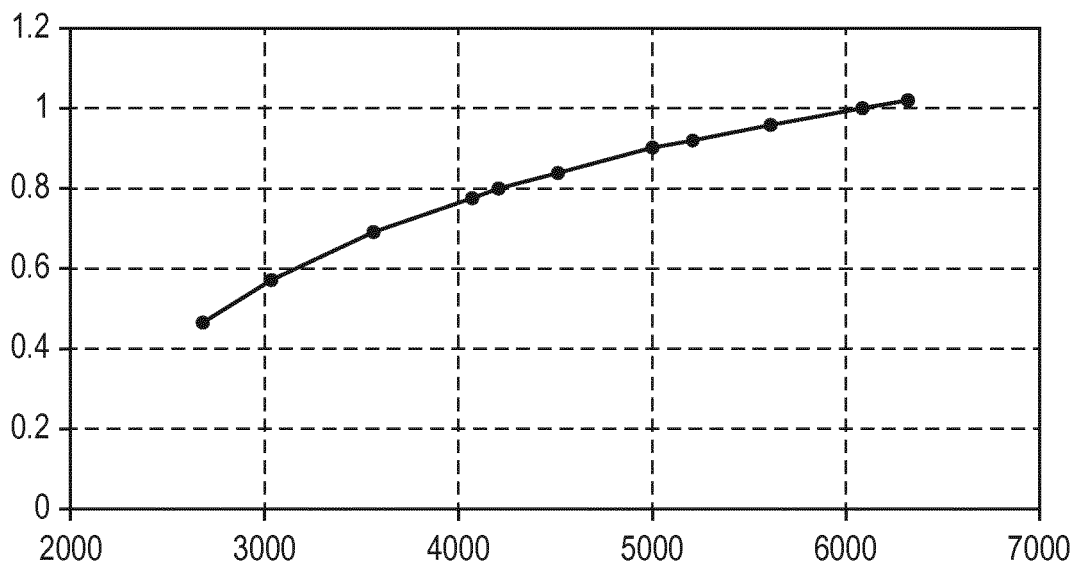
FIG. 5 is a graph showing melanopic weighting factor as a function of color temperature.

Alternatively, melanopic weighting factors for intermediate color temperatures may be determined with more accuracy using the graph shown in FIG. 5. The graph provides a curve of melanopic weighting factor (y-axis) vs color temperature (x-axis). The melanopic weighting factor for any color temperature spanned by the curve may be determined by simply reading off values from the graph.

Figure 6:
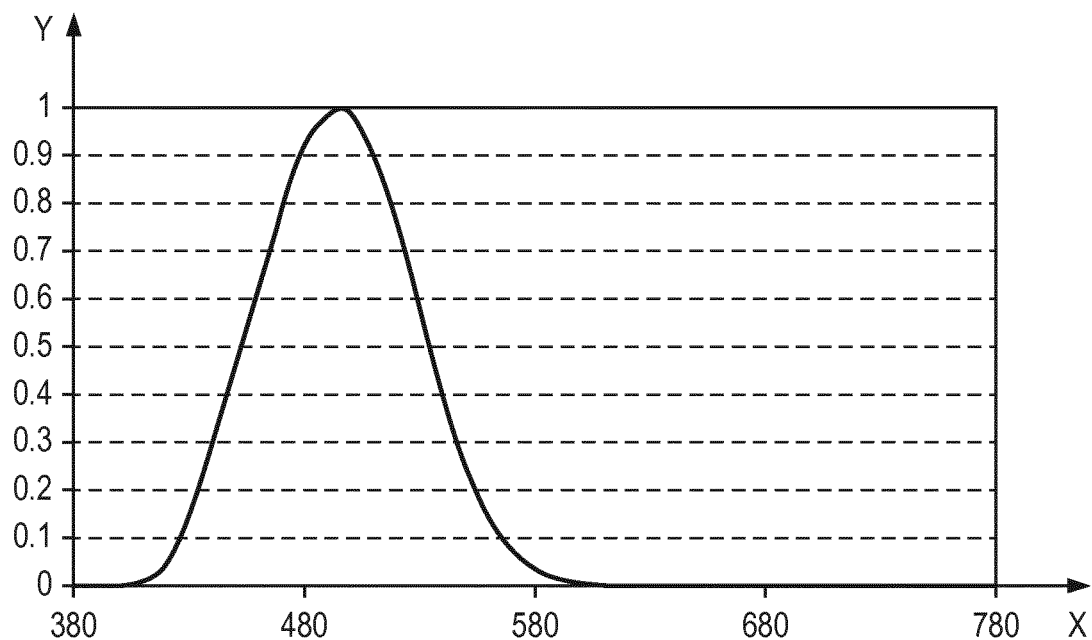
FIG. 6 is a graph showing melanopic weighting factor as a function of wavelength of light.

Both the values in Table 3 and the relationship illustrated in the graph have been determined based on research into the varying melanopic effects of light of differing monochromatic wavelengths. This research has showed that a clear relationship may be established between the wavelength of light and its biological effect upon the human circadian rhythm. FIG. 6 shows the trend that has been established, with the y-axis showing the relative melanopic effect and the x-axis showing wavelength (units: nm). This graph has been taken from the German Institute for Standardisation (DIN) publication "DIN SPEC 5031-100: Optical radiation physics and illuminating engineering—Part 100: Melanopic effects of ocular light on human beings—Quantities, symbols and action spectra" (page 16). The values used for the graph are shown in tabular form in the same document in Appendix C (pages 27-29).

As will be well known to the skilled person, color temperature of a light source refers to the temperature of an ideal black body radiator that radiates light of comparable color to that of the light source. The black body emission spectrum of light of a given temperature is readily derivable from first principles using Planck's law of black body radiation for instance, though the spectra in the context specifically of light chromaticity have been well established independently in their own right and form part of the common general knowledge in the present field.

Using the relationship shown in the graph of FIG. 6, and the known spectral composition of light of different color temperatures, the melanopic weighting factor for light of any color temperature may be derived from first principles by simply calculating a weighted sum of the melanopic factors of each of the spectral components of the light, weighted by their relative amplitude or intensity in the spectral composition.

As discussed above, the controller 24 of the control unit 20 is configured to receive, preferably via the user interface 26, a data input 28 indicating a target melanopic luminous exposure for administration by the lighting system 12.

The controller is then configured to generate a control schedule for appropriately controlling the lighting assembly 16 to deliver the target luminous exposure (after adjustment to account for the additional melanopic luminous exposure of the visual display means 48). Where the lighting assembly 16 has a controllable color temperature, this control schedule may be generated based in part upon the melanopic weighting factors retrieved from a data store (in the example of FIG. 1, the second data store 32), In accordance with an advantageous set of embodiments, the controller 24 is adapted to generate each control schedule based on a pre-stored control schedule template. One or more suitable schedule templates may for instance be stored in a local data store. For the purposes of the example of FIG. 1, these are taken to be stored in the third data store 34 of the control unit 20.

Figure 7:
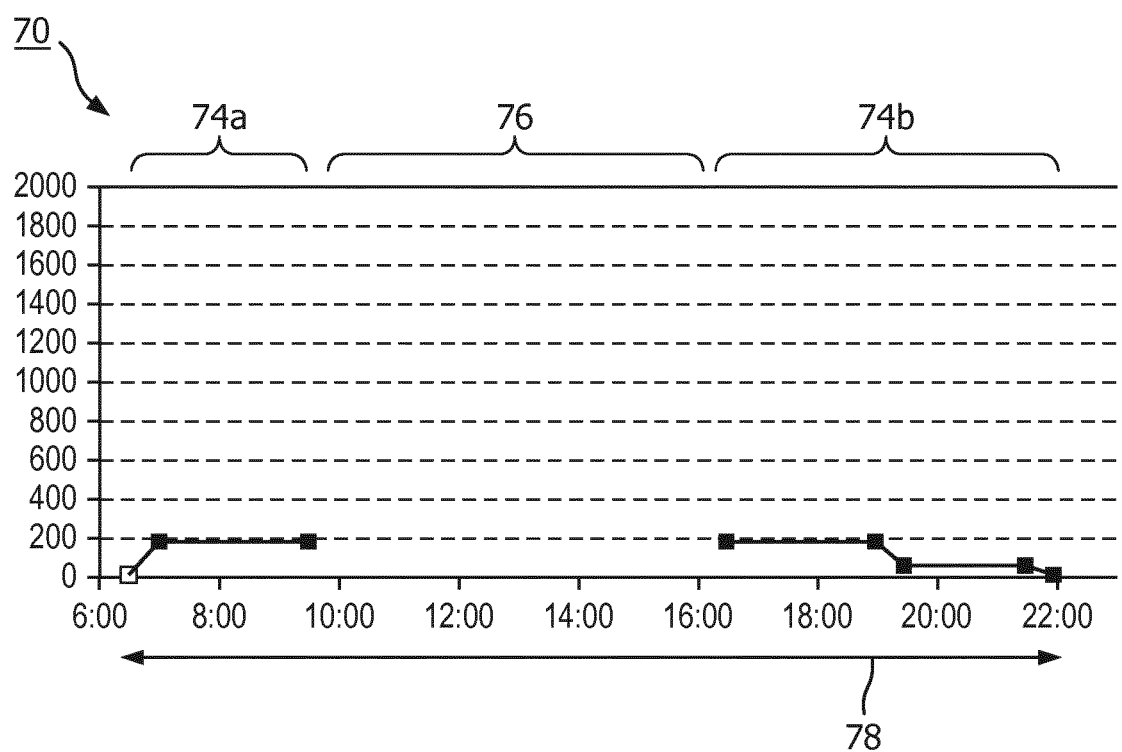
FIG. 7 depicts in graphical form an example control schedule template.

FIG. 7 schematically illustrates in graphical form an example control schedule template 70. The template is presented in the form of a (incomplete) line graph showing illuminance (y axis; units [Lux]) as a function of time (x axis; hours). The template comprises a fixed temporal portion 74, which is pre-configured and formed of the combination of a beginning section 74a and an end section 74b, and a configurable temporal portion 76 for generation by the controller 24. The fixed temporal portion is pre-determined and follows a fixed pattern or curve of illuminance against time. The configurable temporal portion is configurable by the controller, based upon the required melanopic luminous exposure.

Figure 8:
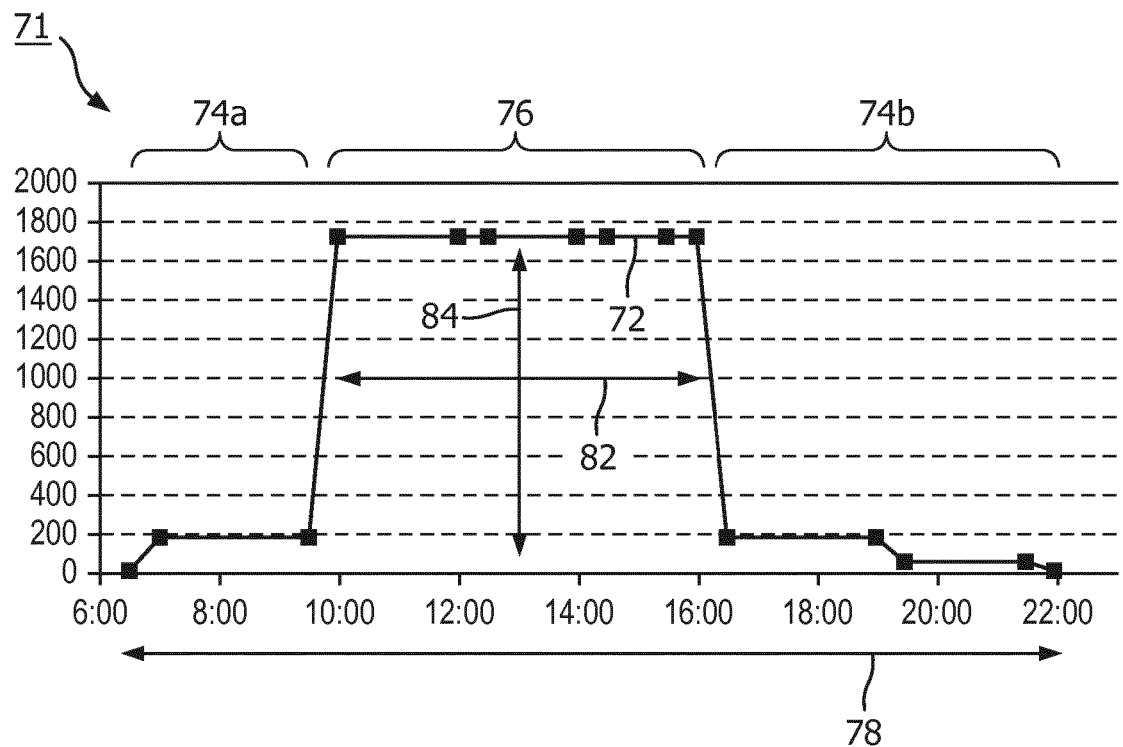
FIG. 8 depicts in graphical form an example control schedule.

The controller 24, upon retrieval of the template 70 generates the configurable temporal portion 76 to thereby create a full control schedule, formed of the fixed portion 74 and the configurable portion. The full schedule in this example extends for a total treatment period 78 of 16 hours, from 06:00 to 22:00. This is illustrated in FIG. 8 which shows in graphical form (at least the illuminance values of) a full control schedule 71 for the duration of the treatment period 78. The full control schedule 71 forms a continuous treatment 'curve' 72 extending from the beginning to the end of the treatment period.

As can be seen from FIG. 8, the fixed portion 74 provides a low-level baseline light output, while the configurable portion 76 provides the substantive part of the luminous exposure, comprising a light output of significantly higher illuminance than that the fixed portion. For this reason, the configurable portion may in descriptions to follow be referred to as a 'boost' portion.

When creating a control schedule 71 for controlling the lighting assembly 16, the controller 24 retrieves from the third data store 34 a control schedule template 70 such as that shown in FIG. 7 and configures the configurable temporal portion 76 such that in total over the complete treatment period 78, the adjusted target melanopic luminous exposure is delivered. In preferred examples, both a duration 82 and maximum illuminance level 84 of the configurable portion 76 are configurable. In some examples, the total duration of the treatment period 78 is fixed, such that adjusting the duration of the configurable portion results in a corresponding alteration to the total duration of the fixed portion 74. However, in further examples, the treatment period 78 may be extendable, in which case extending or reducing the duration of the configurable portion results simply in commensurate extension or reduction of the total treatment period.

The graphical representation of template 70 and completed control schedules 71 of FIGS. 7 and 8 show only variations in illuminance values (y-axis) over time. However, the schedule template 70 and completed schedule 71 may in examples also both include color temperature values, including fixed color temperature values during the fixed temporal portion 74 and configurable values during the configurable portion 76.

This is shown more clearly in Table 4 below, which shows in tabular form an example control schedule template for an example system 12 in which the color temperature of the lighting assembly 16 is configurable. The table shows that during the pre-configured start and end portions 74a and 74b, illuminance and color temperature each marginally increase during the beginning section 74a and decrease during the end section 74b. In particular the illuminance linearly increases from 0 Lux at 06:30 hours to 300 Lux at 07:00 hours. The color temperature gradually increases from 2700 Kelvin to 3000 Kelvin during this time.

Dashed cells in Table 4 indicate parameter values which are configurable by the controller. Upon initially retrieving the template, these values are blank, and must be calculated by the controller to deliver adjusted target melanopic luminous exposure. The thus completed template forms the full control schedule.

TABLE 4

| Start Time | End Time | Start Illuminance [Lux] | End Illuminance [Lux] | Start Color Temperature [Kelvin] | End Color Temperature [Kelvin] |
|---|---|---|---|---|---|
| 00:00 | 06:30 | 0 | 0 | 2700 | 2700 |
| 06:30 | 07:00 | 0 | 300 | 2700 | 3000 |
| 07:00 | 07:30 | 300 | 300 | 3000 | 3000 |
| 07:30 | — | 300 | — | 3000 | — |
| — | — | — | — | — | — |
| — | 17:30 | — | 300 | — | 3000 |
| 17:30 | 19:00 | 300 | 300 | 3000 | 3000 |
| 19:00 | 19:30 | 300 | 100 | 3000 | 2700 |
| 19:30 | 22:00 | 100 | 100 | 2700 | 2700 |
| 22:00 | 00:00 | 0 | 0 | 2700 | 2700 |

There will now be described in detail one example implementation of the system to create a control schedule and administer a light therapy program. This example should not be construed as limiting of the broad general scope of the invention as defined in the claims, but merely provides an illustration one possible implementation.

In accordance with at least one set of embodiments, implementation of the system 12 consists of three phases: an initial configuration phase, a light therapy prescription phase, and a light therapy execution phase.

During the initial configuration phase, a clinician or other user may configure certain boundaries or constraints for parameters of the configurable portion 76 of the control schedule template(s) 70. For example, a clinician may wish to set upper and lower limits for the duration 82 of the configurable portion 76 of the control schedule 71 and/or upper and lower limits of the illuminance 84 during the configurable portion. Table 5 below shows an example set of such constraints. The table represents an example light therapy configuration table which might be stored in one of the data stores 30, 32, 34 of the control unit 20 in which the user has by way of example indicated that the duration of the configurable portion should be constrained to between 2 and 10 hours and the maximum illuminance level to between 500 and 2000 Lux (note that 2000 Lux is in this case in any event the maximum achievable illuminance for the present example lighting assembly—see Table 2).

TABLE 5

| Parameter | Minimum | Maximum |
|---|---|---|
| Configurable Temporal Portion Duration [Hours] | 2 | 10 |
| Illuminance Level [Lux] | 500 | 2000 |

Additionally, according to the present example, during the initial configuration phase, the controller 24 of the control unit 20 may calculate, based on the light therapy constraints set by the clinician (Table 5) and the melanopic weighting factors stored in the second data store 32 (Table 3) minimum and maximum possible melanopic luminous exposures deliverable by the lighting assembly 16 for each of a set of different light output color temperatures. These are then stored in the first data store 30 in the form of a melanopic luminous exposure table.

An (extract of) an example such table is provided by Table 6 below. It indicates for example that with a color temperature of 5000 Kelvin, the deliverable melanopic luminous exposure ranges from 903 LuxHours to 18060 LuxHours. These values are calculated from the information given in the melanopic factor table (Table 3) and the light therapy curve configuration table (Table 5). The minimum deliverable luminous exposure is 500 Lux×2 Hours=1000 Lux-Hours. The maximum luminous exposure is 2000 Lux×10 Hours=20000 LuxHours.

By then applying the relevant melanopic factor (0.903 for a color temperature of 5000 Kelvin according to Table 3) as correction factor, a color-corrected melanopic luminous exposure range is derived as indicated in Table 6. In particular, the minimum melanopic luminous exposure is 0.903×1000 LuxHours=903 LuxHours. The maximum melanopic luminous exposure is 0.903×20000 LuxHours=18060 LuxHours.

TABLE 6

| Color Temperature [Kelvin] | Minimum Melanopic Luminous Exposure [LuxHours] | Maximum Melanopic Luminous Exposure [LuxHours] |
|---|---|---|
| 2602 | 456 | 9120 |
| 2635 | 461 | 9220 |
| 2670 | 469 | 9380 |
| . . . | . . . | . . . |
| 4002 | 780 | 15600 |
| . . . | . . . | . . . |
| 5000 | 903 | 18060 |
| . . . | . . . | . . . |
| 6501 | 1035 | 20700 |

Upon generation of the light therapy configuration table (Table 5) and melanopic luminous exposure table (Table 6), the initial configuration phase is complete. The light therapy prescription phase then follows.

In the light therapy prescription phase, the clinician prescribes a desired light therapy by means for instance of the user interface 26 of the control unit 20. An example user interface is illustrated schematically in FIG. 2 which shows the control unit 20 positioned adjacent a patient bed 66. The unit in this example comprises a display 67 which acts a user output device of the user interface. The unit also comprises a means for user input. This may be a separate keyboard or other input device for instance, or the display may be a touch display enabling user input.

Example steps for interacting with a clinician to receive a light therapy prescription may be as follows.

Firstly, the controller 24 retrieves the minimum and maximum deliverable melanopic luminous exposures from the melanopic luminous exposure table (see Table 6) stored in the first data store 30, and displays these on the display 67.

The user (e.g. clinician) may then select, using the user interface 26, a melanopic luminous exposure to be administered. This is will be the target melanopic luminous exposure. By way of example, consider that the user selects a target luminous exposure of 15600 LuxHours.

Following this, the selected target melanopic luminous exposure is adjusted based on a calculated additional melanopic luminous exposure associated with the visual output of the visual display means. This procedure is described in detail above and will not be repeated here. This results in an adjusted target melanopic luminous exposure.

Following this, the controller 24 determines and displays the minimum and maximum possible color temperatures for light delivered by the lighting assembly, based on the adjusted target melanopic luminous exposure. This is calculated using the stored melanopic luminous exposure table (Table 6). It can be seen from the table that a luminous exposure of 15600 LuxHours requires a color temperature of at least 4002 Kelvin.

The user may then select the preferred color temperature. By way of example, consider that the user selects a color temperature of 5000 Kelvin.

It is noted that although in the present example, the user at this stage is presented only with the option of selecting a preferred color temperature, in other examples, the controller may calculate minimum and maximum deliverable values for any one or more of the parameters: color temperature, duration 82 of the configurable portion 76 of the control schedule, and illuminance level 84 of the light output during the configurable portion. Any or all of these may be displayed to the user via the display 67, and the user given the option of selecting a preferred value for one or more of the parameters.

Returning to the present example, after receipt of a preferred color temperature value, the controller 24 then determines and displays the possible minimum and maximum durations for the configurable portion 76 of the control schedule. The possible values are determined based on the indicated adjusted target melanopic luminous exposure and preferred light color temperature, and are calculated by reference to the melanopic luminous exposure table (Table 6), the light therapy curve configuration table (Table 5), and the melanopic factor table (Table 3).

For the present example, it was assumed that a preferred color temperature of 5000 Kelvin was selected. The minimum possible duration of the configurable temporal portion 76 is calculated by assuming that the maximum illuminance level of 2000 Lux is applied uniformly throughout this temporal portion: 15600 LuxHours/(2000 Lux*0.903)=8.6 Hours.

The maximum possible duration of the configurable temporal portion 76 is calculated by assuming that the minimum illuminance level of 500 Lux is applied uniformly throughout the temporal portion: 15600 LuxHours/(500 Lux*0.903) =34.6 hours. However, since in the initial configuration phase, the user (in this example) constrained the maximum duration of the configurable temporal portion of the control schedule to 10 hours (see Table 5), the maximum duration is capped at 10 hours.

The controller 24 may also concurrently at this stage determine and display the minimum and maximum possible illuminance levels for the configurable portion of the control schedule. These are based again on the adjusted target melanopic luminous exposure and the received preferred color temperature, and are calculated using the melanopic luminous exposure table (Table 6), the light therapy configuration table (Table 5), and the melanopic weighting factor table (see Table 3). For simplicity of calculation, in accordance with at least some examples, the controller may create the control schedule such that a uniform illuminance of light is delivered throughout the duration 82 of the configurable portion 76 of the control schedule 71.

The minimum illuminance level is calculated by assuming that the maximum duration 82 for the configurable temporal portion 76 of 10 hours is applied: 15600 LuxHours/(10 hours*0.903)=1728 Lux. The maximum illuminance level is calculated by assuming that the minimum duration of 2 hours is applied: 15600 LuxHours/(2 hours*0.903)=8638 Lux. However, since the user configured the maximum illuminance level to be 2000 Lux, the maximum is capped at 2000 Lux.

The thus calculated maximum and minimum possible illuminance levels and durations of the configurable portion 76 of the control schedule 71 are displayed using the display 67 of the user interface 26. The user may then input either a preferred duration or a preferred illuminance level. If the user inputs a preferred duration, then the controller 24 calculates a corresponding appropriate illuminance level for delivering the adjusted target melanopic luminous exposure, based on the input duration. If the user inputs a preferred illuminance level, the controller likewise calculates a corresponding appropriate duration for delivering the target luminous exposure, based on the input illuminance level.

It is noted that although in the present example, the controller is configured to concurrently calculate and display maxima and minima for both the configurable portion duration and illuminance level, in further examples, only one of these may be determined and displayed. Which is calculated and displayed may be set by a user as part of the initial configuration phase in accordance with one or more examples.

For the purposes of the present example, it is assumed for illustration that the user selects a preferred duration for the configurable portion 76 of the control schedule 71 of 9 hours. The required illuminance level may then can be calculated as follows: 15600 LuxHours/(9 hours*0.903)= 1920 Lux. This assumes that a uniform illuminance level is to be applied throughout the duration 82 of the configurable portion 76 of the schedule.

Based on the totality of the input preferred parameter values and the calculated parameter values, and based also on the fixed parameter values during the fixed temporal portions 74a, 74b of the control schedule template 70, the controller 24 creates a control schedule for the illuminance and color temperature values of the lighting assembly 16 across the duration of the treatment period 78. The full created schedule in accordance with the illustrative values presented in the above example is shown by Table 7 below.

TABLE 7

| Start Time | End Time | Start Illuminance [Lux] | End Illuminance [Lux] | Start Color Temperature [Kelvin] | End Color Temperature [Kelvin] |
|---|---|---|---|---|---|
| 00:00 | 06:30 | 0 | 0 | 2700 | 2700 |
| 06:30 | 07:00 | 0 | 300 | 2700 | 3000 |
| 07:00 | 07:30 | 300 | 300 | 3000 | 3000 |
| 07:30 | 18:00 | 300 | 1920 | 3000 | 5000 |
| 08:00 | 17:00 | 1920 | 1920 | 5000 | 5000 |
| 17:00 | 17:30 | 1920 | 300 | 5000 | 3000 |
| 17:30 | 19:00 | 300 | 300 | 3000 | 3000 |
| 19:00 | 19:30 | 300 | 100 | 3000 | 2700 |
| 19:30 | 22:00 | 100 | 100 | 2700 | 2700 |
| 22:00 | 00:00 | 0 | 0 | 2700 | 2700 |

Where the control schedule includes different color temperature values (such as in the example presented above), then having thus created the control schedule of Table 7 for the light therapy, the controller 24 is configured to determine for each color temperature of light throughout the control schedule appropriate power levels of each of the LED modules 40, 42 of the lighting assembly 16 necessary to achieve those light color temperatures. These power levels are preferably determined based on an appropriate color temperature table pre-stored in the first data store 30 (for the example lighting assembly in the system of FIG. 1, see Table 1 above).

As noted above, the power levels may in accordance with one or more examples be codified using the DALI addressing protocol. Table 8 shows an example such set of (DALI) power levels for the cold white 40 and warm 42 LED modules of the lighting assembly 16 of the example system of FIG. 1, based on the color temperature values of the example control schedule of Table 7 above. The color temperature table of Table 1 has been used to calculate the necessary DALI light levels for each light color temperature.

TABLE 8

| Start Time | End Time | Start (DALI) Light Level-Cold White LED Modules | End (DALI) Light Level-Cold White LED Modules | Start (DALI) Light Level-Warm LED Modules | End (DALI) Light Level-Warm LED Light Modules |
|---|---|---|---|---|---|
| 00:00 | 06:30 | 0 | 0 | 0 | 0 |
| 06:30 | 07:00 | 0 | 42 | 0 | 213 |
| 07:00 | 07:30 | 42 | 42 | 213 | 213 |
| 07:30 | 18:00 | 42 | 190 | 213 | 65 |
| 08:00 | 17:00 | 190 | 190 | 65 | 65 |
| 17:00 | 17:30 | 190 | 42 | 65 | 213 |
| 17:30 | 19:00 | 42 | 42 | 213 | 213 |
| 19:00 | 19:30 | 42 | 2 | 213 | 253 |
| 19:30 | 22:00 | 2 | 2 | 253 | 253 |
| 22:00 | 00:00 | 0 | 0 | 0 | 0 |

As stated, the set of DALI light levels of Table 8 above have been calculated based on the color temperature table of Table 1. However, the values of this table were calculated based upon the assumption that the lighting assembly 16 is operating a maximum illuminance, i.e. 2000 Lux (see Table 2 above).

For the present example, the illuminance is lower than the maximum of 2000 Lux, and hence a correction must be applied to the power levels of Table 8.

To this end, the controller 24 may calculate the ratio between the illuminance level during the configurable portion 76 of the control schedule 71 and the maximum illuminance of the lighting assembly during this time period. This is then applied to the DALI light level values of Table 8 corresponding to the configurable temporal portion as a correction factor. The resulting final DALI light level schedule is shown in Table 9 below.

TABLE 9

| Start Time | End Time | Start (DALI) Light Level-Cold White LED Modules | End (DALI) Light Level-Cold White LED Modules | Start (DALI) Light Level-Warm LED Modules | End (DALI) Light Level-Warm LED Light Modules |
|---|---|---|---|---|---|
| 00:00 | 06:30 | 0 | 0 | 0 | 0 |
| 06:30 | 07:00 | 0 | 6 | 0 | 32 |
| 07:00 | 07:30 | 6 | 6 | 32 | 32 |
| 07:30 | 18:00 | 6 | 182 | 32 | 62 |
| 08:00 | 17:00 | 182 | 182 | 62 | 62 |
| 17:00 | 17:30 | 182 | 6 | 62 | 32 |
| 17:30 | 19:00 | 6 | 6 | 32 | 32 |
| 19:00 | 19:30 | 6 | 0 | 32 | 13 |
| 19:30 | 22:00 | 0 | 0 | 13 | 13 |
| 22:00 | 00:00 | 0 | 0 | 0 | 0 |

For the present example, during the configurable temporal portion 76, the illuminance level was set at 1920 Lux. The correction factor for values during this portion of the schedule is therefore 1920 Lux/2000 Lux=0.96. The resulting DALI light level for the cold white LED modules 40 during the configurable portion of the schedule is 190*0.96=182. The resulting DALI light levels for the warm LED modules 42 during the configurable portion is 65*0.96=62.

The same correction process for the fixed temporal portion 74 of the control schedule must also be performed. The illuminance during this portion varies, and is in all cases significantly lower than the illuminance throughout the configurable temporal portion 76. Calculation of the correction factors for every illuminance level during the fixed portion will not be exhaustively iterated here, since it will be obvious the skilled person how to perform the necessary calculations. By way of a single example, the illuminance at 07:00 hours is 300 Lux. The correction factor is thus 300/2000=0.15. Applying this correction factor to the DALI light levels of Table 8 for 07:00 yields a value of 6 (=42*0.15) for the cold white LED modules 40 and 32 (=213*0.15) for the warm LED modules 42.

In accordance with at least some examples, the corrected DALI light levels for the fixed temporal portions of each control schedule template 70 may be pre-calculated and stored in the first data store 30 for each lighting assembly compatible with the lighting system. This is possible since the illuminance levels during the fixed portion are pre-set. Pre-storing the corrected DALI light levels for each control schedule template may increase processing efficiency of the system in creating each complete control schedule 71.

Once the corrected light level schedule is derived, as in the example of Table 9, this may be stored, for example in the third data store 34.

The light therapy prescription phase is then complete. The final phase is the light therapy execution phase in which the created control schedule is executed.

In accordance with this phase, the controller 24 is configured to control the lighting assembly 16 to vary the light levels of the LED modules 40, 42 in accordance with the derived light level schedule (Table 9).

To this end, according to one or more embodiments, the controller 24 is adapted to perform the following series of steps recurrently (i.e. at regular time intervals):
1. Retrieve or read the stored light level schedule (Table 9).
2. Determine the current time.
3. Identify the row of the light level schedule corresponding to the current time and thus identify the required DALI light level for the cold white LED Modules 40 and the warm white LED Modules for the current time. (If the lighting assembly does not have controllable color temperature, the required DALI light level for simply the single-color LED module(s) is identified.) In the case that the current time is between time points of the light level schedule, the controller may be adapted to assume that the light level should linearly increase or decrease between time points. For example, with reference to Table 8, if the time were 07:45, the light level for the cold white LED modules 40 would be set half way between 6 and 182, i.e. at a level of 94. The warm LED modules 42 would be set halfway between 32 and 62, i.e. at 47.
4. Communicate the required light level for each of the LED modules 40, 42 for the given point in time to the lighting assembly controller 44.

The lighting assembly controller 44 then instructs the driver module 46 of the lighting assembly in accordance with the received required light level. The driver module (in the present case a DALI driver module) then controls the LED modules 40, 42 accordingly.

The controller may be adapted to repeat the above series of steps by way of non-limiting example, every 10 seconds, or every 30 seconds, or every 5 seconds, depending upon how closely the different time points of the control schedule are spaced.

In accordance with one or more embodiments, the lighting system 12 may further comprise one or more sensors for providing feedback in controlling the lighting assembly or in creating the control schedule 71. By way of example, the example lighting assembly of FIG. 1 comprises an assembly 50 of such sensors, which include a presence sensor 54, an eye status sensor 56 and a light level sensor 58. The sensors may for example facilitate a feedback loop, wherein the control schedule may be adjusted in accordance with readings from the sensor(s). Other example lighting systems 12 may comprise none of these sensors or may comprise a subset of one or more of these sensors, as well as optionally further additional or alternative sensors. More than one of any given type of sensor may be provided.

A presence sensor 54 in accordance with examples may be provided operatively coupled with the controller 24 and arranged in use to detect whether a patient is present within the vicinity of the lighting assembly. The presence sensor may be adapted to detect the presence or absence of a user (such as a patient) in a light output path of the lighting assembly 16. The trajectory of the light output path of the lighting assembly may be known in advance (for instance where the system has a fixed spatial arrangement), in which case the presence sensor can be arranged having a fixed field of view directed toward the projection location of the lighting assembly. For example, with reference to FIG. 2, it would be known that the light output path of the lighting arrangement 16 is towards the patient bed 66. In this case, a presence sensor may be arranged having a field of view directed toward at least a sub-region of the bed.

The controller may be adapted to pause execution of the control schedule upon detecting that the patient is absent, and to continue the control schedule upon detecting that the patient has returned. This would ensure that portions of the scheduled treatment are not missed and the patient receives the full (adjusted) target melanopic luminous exposure.

Alternatively, the controller 24 may be adapted to adjust a duration of, and/or the illuminance and/or color temperature of, the light output during at least a configurable temporal portion of the control schedule based on readings from the sensor in order to ensure delivery of the adjusted target luminous exposure. The schedule 71 may be extended or the illuminance increased during the configurable portion 76 such that the patient, assuming they remain present for the remainder of the adjusted schedule, receives the full (adjusted) target melanopic luminous exposure.

In accordance with one or more examples, the system may include an eye status sensor 56 adapted to detect whether the eyes of a patient are open or closed. This may be an eye tracking sensor, or may be camera or may be a different kind of optical sensor or may be any other form of sensor suitable for the stated purpose, such as ultrasound or acoustic sensor. The sensor may be operable to detect only changes in eye status (i.e. not the absolute status) and so may need calibrating. Alternatively, the sensor may be operable to detect at any given moment whether a patient's eyes are open or closed.

The controller may be configured to adjust the control schedule based on readings from the sensor. For example, the controller may pause execution of the control schedule upon detection that a patient's eyes are closed and continue execution of the control schedule upon detection that the patient's eyes have re-opened.

Alternatively, at least a configurable portion 76 of the control schedule 71 may be extended in duration, or an illuminance level increased during the configurable portion, to compensate for time that a patient's eyes are detected as being closed.

In particular, the controller 24 may be adapted to adjust a duration of, and/or the illuminance and/or color temperature of, the light output during at least a configurable temporal portion of the control schedule based on the readings from the sensor in order to ensure delivery of the target luminous exposure.

The controller 24 may be adapted to calculate, based on readings from the eye status sensor over a defined sensing period, an aggregate time period for which a user's eyes have been closed, and to extend the duration of at least a configurable temporal portion of the control schedule by said aggregate time period.

Additionally or alternatively to readings from an eye sensor, the controller 24 may optionally be adapted to communicate with an associated patient monitoring system. The patient monitoring system may store or otherwise be adapted to provide to the controller information concerning other treatment or medication being administered to the patient or other physiological parameters of the patients. An example patient monitoring system is illustrated schematically in FIG. 1.

According to one or more examples, the system may comprise a light sensor for detecting a level of light proximal to or at the position of a patient to whom the light therapy is to be administered. Preferably, the sensor is positioned or adapted to sense a light level at a position proximal to the patient's eye. In accordance with some examples, the controller 24 may be adapted to increase the illuminance of the light output of the lighting assembly 16 in response to detection that the light level at the patient's eye is lower than that specified in the control schedule for the given moment in time, and vice versa to decrease the light level if the measured level is higher than the expected level for that time. In the latter case, reduction of the illuminance may avoid an overdose of light which may be harmful for the patient, or may affect the effectiveness of the treatment. The sensor allows the illuminance of the lighting assembly to be adjusted according to environmental light levels for example, so that large amounts of external light can be compensated for by lowering the illuminance of the lighting assembly.

According to examples more generally, the controller may be adapted to adjust a duration of, and/or the illuminance and/or color temperature of, the light output during at least a configurable temporal portion of the control schedule based on readings from the sensor, in order to ensure delivery of the target luminous exposure, and optionally wherein the light level sensor is arranged proximal to a user's eye or eyes.

In accordance with one or more examples, the light therapy system 12 may include all three of the above described sensors. A combination of all three may enable the system to derive an approximate measure of the actual melanopic luminous exposure received by the patient. The three sensors together are able to account for moments of absence of the patient, as well as moments at which the patient is present but their eyes are closed, as well as a measured level of the light being received at the position of the patient.

Such a combination of parameters enables more accurate delivery of a required (adjusted) target melanopic luminous exposure. For instance, as noted above, the therapy schedule may be adjusted in dependence upon the readings from the sensors such that the target melanopic exposure may be more accurately delivered.

In the example of FIG. 1 above, the lighting assembly 16 was taken to comprise two sets of LED modules: cold white LED modules, and warm LED modules. However, in accordance with further examples, a different lighting assembly may be used. A lighting assembly may be used comprising only a single type of LED module (e.g. only cold or only warm light). A lighting assembly may be used comprising more than two types of LED modules, for example, three or four or more than four (e.g. cold, warm and medium white LED modules or a combination of different color LEDs).

As emphasized above, the invention is not limited to use of a lighting assembly 16 having a controllable color temperature. In other examples, the lighting assembly is adapted to generate light of only a single fixed color temperature. Controlling the lighting assembly to generate the required light output for executing the control schedule may then comprise controlling an illuminance level of only a single lighting module, or lighting modules of only a single color temperature.

According to one or more examples, using a greater number of LED modules may enable a richer or broader range of light color temperatures to be achieved. This may provide a greater choice to patients as to the particular light color they would prefer, or may provide a greater range of clinical options to the clinician where the color of the light is a clinical factor. Additionally, since the melanopic effect of the light is dependent upon the color, extending the range of color temperatures available to an example lighting assembly may improve the precision with which a desired melanopic luminous exposure can be delivered, or provide greater configuration options for providing a given luminous exposure.

The biological effect of light on the entrainment ("melanopic effect") depends on the length of the light exposure, the intensity of the administered light (i.e. the illuminance) and the color temperature of the light. However, light has only an effect on the circadian rhythm if it is actually received by the photoreceptors in the eye. Therefore, the effect of light depends also on the proportion of time that the eyes are open or closed and the transmittance of the eye lens. It is known that eye lens transmittance decreases with age.

Accordingly, the control schedule 71 may be adapted in accordance with one or more examples in dependence upon the age of the patient. For example, the light level values of the light level schedule of Table 9 or the illuminance values of the control schedule of Table 7 may be adjusted by application of an appropriate age correction factor. The age correction factors may rise for increasing age, so as to increase the applied illuminance for older patients. Similarly, the correction factors may be configured to reduce the applied illuminance for younger patients having a greater lens transmissivity.

An example set of age correction factors is shown in Table 10 below.

TABLE 10

| Patient Age | Age Correction Factor |
|---|---|
| 1 | 0.11 |
| 2 | 0.11 |
| 3 | 0.12 |
| ... | ... |
| 50 | 0.53 |
| ... | ... |
| 75 | 100 |
| ... | ... |
| 100 | 2.14 |

In accordance with one or more examples, the age of the patient may be retrieved from a patient data management system to which the controller is communicatively linked. This is illustrated in FIG. 1 which shows an optional patient data management system 60 comprising an electronic medical record system 62 and patient monitoring system 64. The patient data management system may be external to the light therapy system 12, and simply communicatively linked with the controller 24. The ages of patients may be stored in the electronic medical record system 62.

Figure 9:
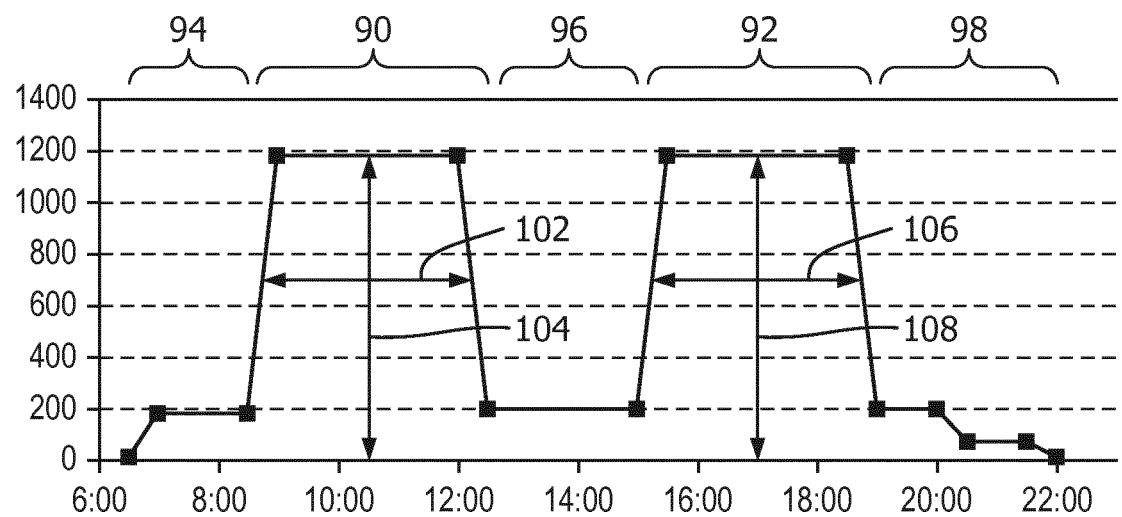
FIG. 9 depicts in graphical form a further example control schedule template.

In examples described above, an example control schedule template 70 was presented comprising a single configurable temporal portion 76 surrounded at either end by a fixed temporal portion 74 being split into two sections 74a, 74b. In accordance with further examples however, different control schedule templates may instead be used. In particular, there may be provided stored in the third data store 34 one or more control schedule templates which include a plurality of configurable temporal portions. An example is shown in graphical form in FIG. 9. The example comprises two configurable portions 90, 92, these being separated by a set of intermediate fixed temporal portions 94, 96, 98. Each of the configurable portions has a separately configurable duration 102, 106 and maximum illuminance level 104, 108. For the purposes of illustration, the configurable portions are shown completed in FIG. 9, although it is to be understood that these portions would in fact be absent in the true template, with the controller adapted to complete them.

In accordance with any example, the fixed temporal portion or portions of the control schedule template, where such a template is used, may take any particular trend or pattern. It is preferred that the average illuminance during the fixed portion(s) is lower than the average illuminance during any of the configurable portions.

Although in examples above, the control schedule is created by the controller 24 based upon a control schedule template 70, in alternative examples, no such template may be used. Illuminance levels of the schedule throughout the duration of the treatment period 78 are set by the controller such in total over the treatment period, the adjusted target melanopic luminous exposure is delivered by the lighting arrangement.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light therapy system, comprising:
a lighting assembly operable to create a light output having a controllable illuminance;
a visual display for presenting a visual output to a user; and
a controller for controlling the lighting assembly to deliver a light therapy treatment, wherein the controller is operatively coupled to the lighting assembly and visual display, and adapted to:
receive a data input indicating a target melanopic luminous exposure for administration of the light therapy treatment by the lighting assembly;
receive a further data input indicative of one or more luminous characteristics of a visual output intended for presentation by the visual display;
determine based on the further data input an estimated additional melanopic luminous exposure associated with the intended visual output;
determine an adjusted target melanopic luminous exposure for administration of the light therapy treatment by the lighting assembly, based on reducing the target melanopic luminous exposure so as to compensate for the additional melanopic luminous exposure;
create, based on the adjusted target melanopic luminous exposure, a control schedule for controlling the illuminance of the lighting assembly over time such as to deliver in total over a defined treatment period the adjusted target melanopic luminous exposure; and
control the lighting assembly in accordance with the control schedule.

2. A light therapy system as claimed in claim 1, wherein the intended visual output of the visual display is associated with an array of constituting pixels, and wherein the further data input includes information indicative of a luminous output of each pixel, and preferably wherein determining the additional melanopic luminous exposure comprises aggregating the luminous outputs of the array of pixels.

3. A light therapy system as claimed in claim 2, wherein determining the additional melanopic luminous exposure is based at least partly on a known relative positioning of each of at least a subset of the pixels, relative to a given user positioning.

4. A light therapy system as claimed in claim 1,
wherein the further data input includes information indicative of a color content of the intended visual output of the visual display, and
wherein determining the additional melanopic luminous exposure comprises applying one or more melanopic weighting factors corresponding to a relative melanopic effect of different wavelengths of light.

5. A light therapy system as claimed in claim 2, wherein the further data input includes information indicative of an illuminance level of each of a set of different light color components of a luminous output of each pixel.

6. A light therapy system as claimed in claim 4, wherein the color content includes each of at least a red, green and blue color component, and wherein the determination of the additional melanopic luminous exposure is based on a simplified color content in which the red component is omitted.

7. A light therapy system as claimed in claim 1, wherein the lighting assembly and the visual display are integrated in a single unit.

8. A light therapy system as claimed in claim 1, wherein the visual output comprises one or more images for presentation to the user.

9. A light therapy system as claimed in claim 1, wherein the visual output comprises one or more video images for presentation to the user.

10. A light therapy system as claimed in claim 1,
wherein the visual output comprises a video image composed of a plurality of image frames, and
wherein determining the additional melanopic luminous exposure comprises determining a melanopic luminous output of each of the image frames and aggregating the determined image frame melanopic luminous outputs.

11. A light therapy system as claimed in claim 10,
wherein each image frame of the video image is associated with an array of constituting pixels, and
wherein the further data input includes information indicative of a luminous output of each of the pixels of each frame, and
wherein determining the melanopic luminous output of each frame comprises aggregating the luminous outputs of the array of pixels associated with the given frame.

12. A light therapy system as claimed in claim 1, wherein the light output of the lighting assembly further has a controllable color temperature.

13. A light therapy system as claimed in claim 12,
wherein the controller is further adapted to retrieve from a data store one or more melanopic weighting factors corresponding to a relative melanopic effect of different color temperatures of light, and
wherein the control schedule is created based on the melanopic weighting values and the adjusted target melanopic luminous exposure, and is for controlling the illuminance and color temperature of the lighting assembly over time such as to deliver in total over the defined treatment period the adjusted target melanopic luminous exposure.

14. A light therapy system as claimed in claim 13, wherein the controller is adapted to further receive color temperature preference data indicating one or more preferred color temperature values, and to create the control schedule such that the color temperature of the light output, for at least a portion of the treatment period, has the preferred color temperature value.

15. A light therapy method comprising controlling a lighting assembly to deliver a melanotic light therapy treatment, the lighting assembly being operable to create a light output having a controllable illuminance, and the method comprising:
receiving a data input indicating a target melanopic luminous exposure for administration of the light therapy treatment by the lighting assembly;
receiving a further data input indicative of one or more luminous characteristics of a visual output intended for presentation by a visual display;
determining, based on the further data input, an estimated additional melanopic luminous exposure associated with the intended visual output;
determining an adjusted target melanopic luminous exposure for administration of the light therapy treatment by the lighting assembly, based on reducing the target melanopic luminous exposure so as to compensate for the additional melanopic luminous exposure;
creating, based on the adjusted target melanopic luminous exposure, a control schedule for controlling the illuminance of the lighting assembly over time such as to deliver in total over a defined treatment period the adjusted target melanopic luminous exposure; and
controlling the lighting assembly in accordance with the control schedule.

* * * * *